US011882630B2

(12) United States Patent
Vissenberg et al.

(10) Patent No.: US 11,882,630 B2
(45) Date of Patent: Jan. 23, 2024

(54) LIGHTING SYSTEM WITH CONSTANT ILLUMINANCE DIMMING

(71) Applicant: SIGNIFY HOLDING B.V., Eindhoven (NL)

(72) Inventors: Michel Cornelis Josephus Marie Vissenberg, Eindhoven (NL); Leonie Maria Geerdinck, Eindhoven (NL); Barry Mos, Bocholt (BE); Lucas Jozef Maria Schlangen, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 235 days.

(21) Appl. No.: 17/426,330

(22) PCT Filed: Feb. 10, 2020

(86) PCT No.: PCT/EP2020/053287
§ 371 (c)(1),
(2) Date: Jul. 28, 2021

(87) PCT Pub. No.: WO2020/169383
PCT Pub. Date: Aug. 27, 2020

(65) Prior Publication Data
US 2022/0110194 A1    Apr. 7, 2022

(30) Foreign Application Priority Data
Feb. 21, 2019  (EP) ..................................... 19158460

(51) Int. Cl.
*H05B 45/10* (2020.01)
*H05B 47/155* (2020.01)
(Continued)

(52) U.S. Cl.
CPC .............. *H05B 45/10* (2020.01); *F21S 6/008* (2013.01); *F21S 8/04* (2013.01); *H05B 47/10* (2020.01);
(Continued)

(58) Field of Classification Search
CPC ...... H05B 45/10; H05B 47/155; H05B 4/105; H05B 47/105; F21S 6/008; F21S 8/04
See application file for complete search history.

(56) References Cited

U.S. PATENT DOCUMENTS 8,373,366 B2    2/2013  Baaijens et al.
9,310,029 B2    4/2016  Kim
(Continued)

FOREIGN PATENT DOCUMENTS

EP    3211972 A1 *    8/2017    .............. F21S 6/008

OTHER PUBLICATIONS

Machine translation of EP-3211972-A1 to Horath, published 2017-08-30 (Year: 2017).*

(Continued)

*Primary Examiner* — William N Harris

(57) ABSTRACT

The invention provides a lighting system (100) comprising a first light source (10), a second light source (20), and a control system (30), wherein: —the first light source (10) is configured to generate first light source light (11) with a controllable first radiant flux, wherein the first radiant flux is dimmable over a first dimming range; wherein the first light source light (11) has a first angular distribution relative to the lighting system (100); —the second light source (20) is configured to generate second light source light (21) with a controllable second radiant flux, wherein the second radiant flux is dimmable over a second dimming range; wherein the second light source light (21) has a second angular distribution relative to the lighting system (100), different from
(Continued)

the first angular distribution; —the control system (30) is configured to control the first light source (10) and the second light source (20), wherein, in a controlling mode of the control system (30), the control system (30) is configured to control a value of one of the first radiant flux and the second radiant flux with a negative proportional dependence of a change in a value of the other of the first radiant flux and the second radiant flux over at least a respective part of the respective dimming range.

15 Claims, 8 Drawing Sheets

(51) Int. Cl.
    *H05B 47/105*     (2020.01)
    *F21S 6/00*     (2006.01)
    *H05B 47/10*     (2020.01)
    *F21S 8/04*     (2006.01)

(52) U.S. Cl.
    CPC ......... *H05B 47/105* (2020.01); *H05B 47/155* (2020.01)

(56) References Cited

U.S. PATENT DOCUMENTS

| | | |
|---|---|---|
| 9,655,191 B2 | 5/2017 | Vissenberg et al. |
| 9,936,564 B2 | 4/2018 | Choong et al. |
| 10,036,538 B2 | 7/2018 | Goldstein et al. |
| 2012/0206050 A1 | 8/2012 | Spero |
| 2014/0192558 A1* | 7/2014 | Dau .......... G02B 6/00 362/613 |
| 2014/0301077 A1 | 10/2014 | Kim |
| 2015/0211710 A1* | 7/2015 | Speier ........ G02B 6/0055 362/606 |
| 2015/0373806 A1 | 12/2015 | Vissenberg et al. |
| 2016/0143109 A1 | 5/2016 | Lal et al. |
| 2016/0323950 A1 | 11/2016 | Ogg et al. |
| 2017/0175987 A1 | 6/2017 | Newton et al. |
| 2017/0348506 A1 | 12/2017 | Berman et al. |
| 2021/0231855 A1* | 7/2021 | Armbruster .......... G02B 6/0001 |

OTHER PUBLICATIONS

Adler, J.S., Kripke, D.F., Loving, R.T., Berga, S.L. 1992. Peripheral vision suppression 631 of melatonin. J. Pineal Res. 12(2), 49-52.

Glickman, G., Hanifin, J., Rollag, M.D., Wang, J., Cooper, H., Brainard, G.C. 2003. Inferior retinal light exposure is more effective than superior retinal exposure in 666 suppressing melatonin in humans. J. Biol. Rhythms 18 (1):71-9. 667.

Joyce, D.S., Feigl, B., Zele, A. 2016. Melanopsin-mediated post-illumination pupil response in the peripheral retina. J. Vision 16(3):5, 1-15.

Lasko, T.A., Kripke, D.F., Elliot, J.A. 1999. Melatonin suppression by illumination of upper 678 and lower visual fields. J. Biol. Rhythms 14(2), 122-125.

Visser, E.K., Beersma, D.G., Daan, S. 1999. Melatonin suppression by light in humans is 698 maximal when the nasal part of the retina is illuminated. J. Biol. Rhythms 14(2), 116-21.

\* cited by examiner

LIGHTING SYSTEM WITH CONSTANT ILLUMINANCE DIMMING

CROSS-REFERENCE TO PRIOR APPLICATIONS

This application is the U.S. National Phase application under 35 U.S.C. § 371 of International Application No. PCT/EP2020/053287, filed on Feb. 10, 2020, which claims the benefit of European Patent Application No. 19158460.6, filed on Feb. 2, 2019. These applications are hereby incorporated by reference herein.

FIELD OF THE INVENTION

The invention relates to a lighting system. The invention also relates to the use of such lighting system.

BACKGROUND OF THE INVENTION

Lighting systems to illuminate spaces are known in the art. U.S. Pat. No. 9,310,029 B2, for instance, describes a method for illuminating a space, the method using a plurality of LED illumination modules, wherein the plurality of LED illumination modules control a mutual distribution ratio between a vertical illuminance and a horizontal illuminance and provides different vertical illuminance and horizontal illuminance at one point within the space having a constant volume, according to a light distribution condition. The light distribution condition is a control of a radiation angle, or the control of the radiation angle and a division of a light distribution pattern. The radiation angle is 10-90°, and the light distribution pattern is divided into at least two areas.

US2017348506 discloses a lighting system comprising a first light source, a second light source and a controller configured to control the first and second light source with a mutually negative proportional dependence.

SUMMARY OF THE INVENTION

The intensity distributions and positions of luminaires of an indoor lighting system are carefully designed to meet lighting criteria related to, for instance one or more of: required levels of task lighting on a desk; efficiency/luminaire utilization factor (amount of light on the right spot); glare; room appearance (wall and ceiling illuminance values and uniformity); appearance of objects and people in the room (cylindrical illuminance, modelling index, etc.); biological light dose (EML: Equivalent Melanopic Lux, as defined in the WELL building standard), etc. The optimum may depend on the application details.

An example of a design trade-off may e.g. be the ratio between direct (down) lighting and indirect (up) lighting with suspended luminaires. The direct lighting may have a higher utilization factor and may save energy (must of the light is efficiently focused on the horizontal task area), whereas the indirect light may yield a higher ceiling and wall illuminance, whereby a more pleasant and brighter room appearance may be created.

Furthermore, the indirect light may have a higher EML rating, thus having a stronger biological impact (affecting, e.g., sleep, wellbeing and performance).

Hence, it is an aspect of the invention to provide an alternative lighting system. The present invention may have as object to provide a useful alternative.

When a luminaire is dimmed up or down, all lighting parameters (horizontal task illuminance, wall illuminance, EML, etc.) are altered. As said, different light beams may have different impacts. For instance, direct lighting with an intensity cut-off at high angles may have a relatively strong impact on horizontal illuminance values, but relatively less on vertical illuminance values. For instance, diffuse light (Lambertian, wide beam, or indirect lighting) may have a relatively stronger impact on vertical illuminance values (and relatively less on horizontal illuminance values). The controls for dimming a lighting system or luminaire with more than one type of beam may provide one dimming control per beam type. Drawback is that the user may then need knowledge on how to balance the different light beams such that they add up to produce the intended light distribution in the room.

Hence, in a first aspect the invention provides a lighting system comprising a first light source, a second light source, and optionally a control system, wherein:
the first light source is configured to generate first light source light, especially with a controllable first radiant flux, wherein in embodiments the first radiant flux is dimmable over a first dimming range; wherein the first light source light has a first angular distribution relative to the lighting system;
the second light source is configured to generate second light source light, especially with a controllable second radiant flux, wherein in embodiments the second radiant flux is dimmable over a second dimming range; wherein the second light source light has a second angular distribution relative to the lighting system, which is (in embodiments) different from the first angular distribution;
the (optional) control system is configured to control the first light source and the second light source, wherein, in embodiments a controlling mode of the control system, the control system is configured to control a value of one of the first radiant flux and the second radiant flux with a negative proportional dependence of a change in a value of the other of the first radiant flux and the second radiant flux over at least a respective part of the respective dimming range,
wherein the first light source is configured to generate the first light source light providing one or more of a first horizontal illuminance $E_{h1}$ and first vertical illuminance $E_{v1}$, wherein during operation of both the first and the second light source at equal power the second light source is configured to generate the second light source light providing one or more of a second horizontal illuminance $E_{h2}$ and second vertical illuminance $E_{v2}$, wherein $E_{h1} > E_{h2}$, and wherein $E_{v2} > E_{v1}$.

With such lighting system, it is e.g. possible to dim one of the light sources, or to increase the power of one of the light sources, for specific purposes like e.g. providing a minimum level or maximum level of task lighting, while at the same time automatically controlling the other light source. In embodiments, the other light source may have directly, or indirectly (via reflections at the wall and/or ceiling and/or at the floor and/or at a desk etc.), impact on the irradiance or illuminance provided at one or more positions (in the space) relative to the lighting system. Hence, an automatic coupling may be desirable. Hence, with the present invention, it is e.g. possible to keep in a specific direction or at a specific position desirable lighting properties, while dimming or increasing the power of one of the light sources.

Hence, in embodiments specific directional lighting properties or spatial lighting properties are kept constant while changing the power of one (or both) of the first and second light sources. In further embodiments, e.g. an illuminance is kept constant. The illuminance may have a spatial (position) aspect and a directional (surface orientation and optional angular filter) aspect.

Herein, the terms "dimming" and "dim" and similar terms refer to both options of up dimming (increasing a flux) and down dimming (decreasing a flux).

Hence, amongst others in embodiments herein a lighting system is proposed, especially with at least two separately dimmable beams, (a) wherein in embodiments the two beams may have a different intensity profile (beam width, shape and/or direction) and/or (b) wherein in embodiments the two beams may have a different spectrum, especially at least the former. In this way, the two beams may in embodiments e.g. have different impacts on horizontal and vertical illuminance distributions in the room. Further explanations, embodiments, and examples are provided below.

As indicated above, in an aspect the invention provides a lighting system comprising a first light source, a second light source, and a control system The term "light source" may refer to a semiconductor light-emitting device, such as a light emitting diode (LEDs), a resonant cavity light emitting diode (RCLED), a vertical cavity laser diode (VCSELs), an edge emitting laser, etc. The term "light source" may also refer to an organic light-emitting diode, such as a passive-matrix (PMOLED) or an active-matrix (AMOLED). In a specific embodiment, the light source comprises a solid state light source (such as a LED or laser diode). In an embodiment, the light source comprises a LED (light emitting diode). The term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of semiconductor light sources may be configured on the same substrate. In embodiments, a COB is a multi LED chip configured together as a single lighting module.

The term "light source" may also relate to a plurality of light sources, such as 2-2000 solid state light sources. For instance, the lighting system may comprise a plurality of first light sources and/or a plurality of second light sources. Hence, the term "first light source" may also refer to a plurality of (essentially identical) first light sources. The term "first light source" may also refer a first type of light sources. The term "second light source" may also refer to a plurality of (essentially identical) second light sources. The term "second light source" may also refer a second type of light sources. Essentially identical light sources are configured to generate light source light with essentially identical spectral distributions and spatial distributions of the light source light, like solid state light sources from the same bin.

In embodiments, the light source may comprise one or more micro-optical elements (array of micro lenses) downstream of a single solid state light source, such as a LED, or downstream of a plurality of solid state light sources (i.e. e.g. shared by multiple LEDs). In embodiments, the light source may comprise a LED with on-chip optics. In embodiments, the light source comprises a pixelated single LEDs (with or without optics) (offering in embodiments on-chip beam steering).

However, alternatively or additionally, other type of light sources (for the first light source and/or the second light source) may be applied as well, as high pressure lamps, discharge lamps, incandescent lamps, fluorescent lamps, etc.

For each of the first light source and the second light source, the above may apply. The first light source may differ in type from the second light source, like a halogen lamp and a solid state light source. Especially, however, the first light source and second light source are each solid state light sources.

In embodiments, both the first light source and the second light source are configured to generate white light. In other embodiments, one or more of the first light source and second light source may provide light source light that is color tunable. This is herein further not discussed. Herein, the invention is explained in relation to controlling modes wherein the spectral distribution of the light of the first light source or of the second light source is not necessarily changed. However, such embodiments are herein not excluded. Note that a change in the spectral distribution may also have impact on the proportionality (of the radiant fluxes (and thus illuminances)).

The term "white light" herein, is known to the person skilled in the art. It especially relates to light having a correlated color temperature (CCT) between about 2000 and 20000 K, especially 2700-20000 K, for general lighting especially in the range of about 2700 K and 6500 K, and especially within about 15 SDCM (standard deviation of color matching) from the BBL (black body locus), especially within about 10 SDCM from the BBL, even more especially within about 5 SDCM from the BBL.

As indicated above, both the first light source and the second light source may be configured to generate white light source light (i.e. first light source light and second light source light, respectively). However, these may also differ in the type of light they provide. For instance, the first light source light and the second light source light may differ in one or more of color point and correlated color temperature (CCT). However, in embodiments the first light source light and the second light source light may essentially be the same in terms of one or more of color point and correlated color temperature (CCT), such as less than 10%, especially less than 5% difference in one or more of CIE x coordinate, CIE y coordinate, and color temperature (K). For instance, in embodiments the spectral distributions may be different, but may have essentially the same color point (CIE). In embodiments, the spectral distributions of the first light source light and the second light source light differ especially in the cyan area. In this way different biological doses (EML) may be provided with the different types of light source light. See further also below. The abbreviation "CIE" especially refers to the CIE 1931 RGB color space defined by the International Commission on Illumination (CIE) in 1931, as known to a person skilled in the art.

Even when the light generating means of the first light source and the second light source are essentially identical, such as solid state light sources from the same bin, the intensity distribution of the light source light may be different, like Lambertian, batwing, etc., due to optics used downstream of the light generating means. As indicated above, the combination of a light generating means, like a solid state light source, and optics, may herein also be indicated as "light source". Hence, the light sources may differ in intensity distribution of the light source light (respective to the relevant light source). However, in specific embodiments they may also be the same; see further also below.

Herein, the invention is defined in relation to a first light source and a second light source. However, the principle may also be extended to more than two types of light sources. As within the context of the invention in embodiments horizontal illumination and vertical illumination may be relevant, the light sources may be divided in those one or more light sources that have relatively more impact on one of the horizontal illumination and the vertical illumination, and those one or more other light sources that have relatively more impact on the other of the horizontal illumination and the vertical illumination.

As indicated above, the first light source is especially configured to generate first light source light, especially with a controllable first radiant flux, wherein in embodiments the first radiant flux is dimmable over a first dimming range. Especially, the first light source light has a first angular distribution relative to the lighting system. As indicated above, the second light source is especially configured to generate second light source light, especially with a controllable second radiant flux, wherein in embodiments the second radiant flux is dimmable over a second dimming range. Especially, the second light source light has a second angular distribution relative to the lighting system. In specific embodiments, the second angular distribution is different from the first angular distribution.

Hence, a point may be defined, relative to which the beam of the light source light is defined. Such point may be the point of gravity of a lighting module or luminaire comprising the first light source and the second light source. In specific embodiments, as reference point the (number averaged) geometrical center point of the light emitting surfaces of the light sources may be applied When the first light source and the second light source both provide the light source light in essentially the same direction, the light sources may be available on the same support. For instance, the support, or a plane through the support, or the housing comprising the first light source and the second light source, or a point of gravity of lighting module or luminaire, may be used as reference, or especially the above-mentioned (number averaged) geometrical center point).

Hence, the phrase "the second angular distribution is different from the first angular distribution" and similar phrases does not necessarily imply that the angular distribution of the of the first light source light and the second light source light are different per se; they may also be identical, but the first light source light and second light source light may emanate in different direction. For instance, identical light sources used as uplighter and downlighter in a lighting module or luminaire may have the same angular distributions, but provide different angular distributions relative to the lighting system (or a module or luminaire thereof. Especially, the angular distribution of the intensities of the light sources, relative to the lighting system (especially relative to a module comprising both the first light source and the second light source) are different.

Hence, the first light source and the second light source are comprised by the lighting system. The lighting system may comprise a luminaire or module. Such luminaire or module may comprise the first light source and the second light source. The luminaire or module may comprise a housing. The housing may at least partly comprise the first light source and/or the second light source. The luminaire or module may also comprise the controlling system. However, the controlling system may also be configured external of the module.

Here below, the terms "module" or "luminaire" may refer to the same items.

As indicated above, the first light source may be dimmable and the second light source may be dimmable. Hence, the (first and/or second) light source is dimmable over a dimming range, which is indicated with the phrases "controllable first radiant flux", "the first radiant flux is dimmable over a first dimming range", "controllable second radiant flux", "the second radiant flux is dimmable over a first dimming range", and similar phrases.

Hence, in an aspect the invention also provides a luminaire comprising
the first light source is configured to generate first light source light, especially with a controllable first radiant flux, wherein in embodiments the first radiant flux is dimmable over a first dimming range; wherein the first light source light has a first angular distribution relative to the lighting system;
the second light source is configured to generate second light source light, especially with a controllable second radiant flux, wherein in embodiments the second radiant flux is dimmable over a second dimming range; wherein the second light source light has a second angular distribution relative to the lighting system, which is in embodiments different from the first angular distribution;
optionally the control system is configured to control the first light source and the second light source, wherein, in embodiments a controlling mode of the control system, the control system is configured to control a value of one of the first radiant flux and the second radiant flux with a negative proportional dependence of a change in a value of the other of the first radiant flux and the second radiant flux over at least a respective part of the respective dimming range,
wherein the first light source is configured to generate the first light source light providing one or more of a first horizontal illuminance $E_{h1}$ and first vertical illuminance $E_{v1}$, wherein during operation of both the first and the second light source at equal power the second light source is configured to generate the second light source light providing one or more of a second horizontal illuminance $E_{h2}$ and second vertical illuminance $E_{v2}$, wherein $E_{h1} > E_{h2}$, and wherein $E_{v2} > E_{v1}$.

The term "luminaire" may in embodiments also refer to a plurality of (different) luminaires. For instance, in embodiments the lighting system may (thus) also comprise a plurality of essentially identical luminaires. However, in other embodiments the lighting system may also comprise a plurality of luminaires, with two or more subsets of different luminaires, such as first luminaire(s) comprising the first light source(s) (and not the second light source(s)), and second luminaire(s) comprising the second light source(s) (and not the first light source(s)), though of course other examples may also be possible.

In short, the lighting system may be one of:
a lamp unit comprising the controller and integrated first and second light source;
a single luminaire comprising the controller and a housing accommodating at least one first light source and at least one second light source;
a plurality of first modules comprising only first light sources and second modules comprising only second light sources;
a plurality of lamp units and/or luminaires and at least one controller When a light source has a maximum power, the dimming range may be over e.g. x-y % of the maximum power, wherein x may be 0%, or may be larger than zero (but smaller than 100% and smaller than y), and wherein y is 100% or smaller (but larger than x). In embodiments, the dimming range may be over x-100%, wherein x is 20% or less. This may especially apply to both light sources, though the values of x and y may differ for both light sources. Note that this dimming behavior refers to the dimming of the (first and/or second) light source per se. Below, the coupling of at least part(s) of the dimming range is discussed.

The lighting system further comprises in embodiments a control system. Hence, the light sources are especially functionally coupled to the control system. The control system is configured to control the first light source and the second light source. In other words, the control system is configured to control the first light source light and the second light source light. More especially, the control system is configured to control the first radiant flux and the second radiant flux. Hence, thought it may not be excluded that a user may manually change the first radiant flux and/or the second radiant flux, in general a change will be executed by the control system.

The term "controlling" and similar terms especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. . . . . Beyond that, the term "controlling" and similar terms may additionally include monitoring. Hence, the term "controlling" and similar terms may include imposing behavior on an element and also imposing behavior on an element and monitoring the element. The controlling of the element can be done with a control system, which may also be indicated as "controller". The control system and the element may thus at least temporarily, or permanently, functionally be coupled. The element may comprise the control system. In embodiments, the control system and element may not be physically coupled. Control can be done via wired and/or wireless control. The term "control system" may also refer to a plurality of different control systems, which especially are functionally coupled, and of which e.g. one control system may be a master control system and one or more others may be slave control systems. A control system may comprise or may be functionally coupled to a user interface.

The control system may also be configured to receive and execute instructions form a remote control. In embodiments, the control system may be controlled via an App on a device, such as a portable device like a Smartphone or I-phone, a tablet, etc. . . . . The device is thus not necessarily coupled to the lighting system, but may be (temporarily) functionally coupled to the lighting system.

Hence, in embodiments the control system may (also) be configured to be controlled by an App on a remote device. In such embodiments the control system of the lighting system may be a slave control system or control in a slave mode.

The system, or apparatus, or device may execute an action in a "mode" or "operation mode" or "mode of operation". Likewise, in a method an action or stage, or step may be executed in a "mode" or "operation mode" or "mode of operation". The term "mode" may also be indicated as "controlling mode". This does not exclude that the system, or apparatus, or device may also be adapted for providing another controlling mode, or a plurality of other controlling modes. Likewise, this may not exclude that before executing the mode and/or after executing the mode one or more other modes may be executed.

However, in embodiments a control system may be available, that is adapted to provide at least the controlling mode. Would other modes be available, the choice of such modes may especially be executed via a user interface, though other options, like executing a mode in dependence of a sensor signal or a (time) scheme, may also be possible. The operation mode may in embodiments also refer to a system, or apparatus, or device, that can only operate in a single operation mode (i.e. "on", without further tunability).

Hence, in embodiments, the control system may control in dependence of one or more of an input signal of a user interface, a sensor signal (of a sensor), and a timer. The term "timer" may refer to a clock and/or a predetermined time scheme.

Hence, there may in embodiments be more controlling modes. However, the control system at least provides a controlling mode as defined herein. Therefore, in embodiments the control system is configured to control the first light source and the second light source, wherein, in a controlling mode of the control system, the control system is configured to control a value of one of the first radiant flux and the second radiant flux with a negative proportional dependence of a change in a value of the other of the first radiant flux and the second radiant flux over at least a respective part of the respective dimming range. The term "controlling mode" may thus also refer to a plurality of different controlling modes.

The phrase "to control a value of one of the first radiant flux and the second radiant flux with a negative proportional dependence of a change in a value of the other of the first radiant flux and the second radiant flux" and similar phrases especially indicate that when one of the radiant fluxes increases, the other one will decrease (and vice versa). Likewise, a positive proportional dependence of a change in a value of the other of the first radiant flux and the second radiant flux" would indicate that when one of the radiant fluxes increases, also other one will increase (and vice versa, i.e. when one decreases, also the other decrease). This may be the case in lighting systems wherein a first light source and a second light source are coupled, and with an intensity control the intensity can be controlled of the system light.

Hence, when the first radiant flux is indicated as $W_1$ (Watts) and the second radiant flux is indicated as $W_2$ (Watts), $W_1$ and $W_2$ may relate e.g. as $W_1=W_{1,0}-c_1*W_2$ or $W_2=W_{2,0}-c_2*W_1$. Note that the following may thus apply: $W_{1,0}=W_{2,0}/c_2$ and $c_1=1/c_2$ because both relations describe the same linear relationship between the two fluxes. $W_{1,0}$ and $W_{2,0}$ may be defined as the respective radiant fluxes where the other radiant flux is zero (although these values may lie outside the dimming range and then may not be reached in practice).

Note that when the radiant fluxes are changed, it may be possible that within at least parts of the dimming ranges an illuminance in a position, or averaged over an area, in the space where the lighting system provides the lighting system light may essentially stay constant. This is due to the different angular distributions relative to the lighting system (and/or reflections e.g. at a wall and/or ceiling). The term "lighting system light" refers to the light generated by the lighting system and including one or more of the first light source light and the second light source light. In general, in the controlling mode(s) as defined herein, over substantial parts of the dimming ranges wherein the radiant fluxes are coupled according to the negative proportional dependence, the lighting system light will comprise both the first light source light and the second light source light. Hence, because of the negative proportional relationship between different beam fluxes, in embodiments one of the illuminance values can be kept constant, while the other can be varied.

Hence, $W_1$ may refer to any value within the range of $0-W_{1max}$ of the first light source, wherein $W_{1max}$ is the maximum first radiant flux of the first light source (light). Likewise, $W_2$ may refer to any value within the range of $0-W_{2max}$ of the second light source, wherein $W_{2max}$ is the maximum second radiant flux of the second light source (light).

However, it may not always be possible to couple the radiant fluxes over the entire dimming ranges of both the first radiant flux and the second radiant flux. Hence, in embodiments such relations may apply for a subset of the first radiant fluxes within the first dimming range and/or may apply for a subset of the second radiant fluxes within the second dimming range. Hence, the negative proportional dependence may be over at least parts of the first dimming range and/or the negative proportional dependence may be over at least parts of the second dimming range. Therefore, in embodiments the negative proportional dependence may be over at least a respective part of the respective dimming range. As the dimming ranges are limited between 0% and 100%, and because of the linear relationship between the two, the dimming range according to the invention may now also (at least) be limited when the other channel reaches the hard boundary of 0% or 100%.

Hence, the illuminance may only be kept constant until one of the sources reaches a maximum dimming level or a minimum dimming level. Therefore, the sources may not be used over the full dimming range as a limit may be reached when one of the sources reaches 0% or 100% dimming, in the herein described controlling mode wherein the radiant fluxes (or illuminances, see also elsewhere) are related to each other according to a negative proportional dependence.

The invention is thus especially not related to an array of identical (first and second) light sources with parallel configured optical axes. However, the invention includes—amongst others—embodiments wherein identical (or different types of) light sources are configured with non-collinear optical axes. The term "non-collinear" may also refer to antiparallel, i.e. parallel optical axis, but pointing in opposite directions. The term "optical axis" in relation to a beam of light is known in the art and may e.g. refer to a line or vector starting from a light emitting surface, which indicates the path or direction of the beam. The direction of the vector or line coincides with the symmetry axis of a rotationally or quadrant symmetric luminous intensity distribution. For asymmetric intensity distributions, either the average direction of the luminous intensity distribution is chosen, or the direction of the peak luminous intensity. Instead of the term optical axis, and to indicate directionality, also the term "mean direction vector" may be applied.

Hence, in embodiments the first light source light has a first optical axis, wherein the second light source light has a second optical axis, wherein the first light source and the second light source are configured to provide the first light source light and the second light source light with the optical axes having a mutual angle $\alpha 1 \neq 0°$. When the light sources have optical axes that are not collinear, the angle between the optical axes may in general be substantially larger than $0°$, such as $\geq 45°$. In specific embodiments, the optical axes may have a mutual angle $90° \leq \alpha 1 \leq 180°$. In yet other embodiments, the optical axes may have a mutual angle $45° \leq \alpha 1 \leq 135°$. In yet other specific embodiments, the optical axes may have a mutual angle of $180°$.

In further specific embodiments, especially (but not exclusively) wherein e.g. the optical axes may have a mutual angle of $180°$, the first light source may be configured as downlighter and the second light source is configured as uplighter. The invention is not limited to the application in a space, but relates also to the system per se. However, the system (or luminaire) may be configured such that during application, the first light source may be configured as downlighter and the second light source is configured as uplighter. The downlighter may essentially be used for task lighting, such as working or eating; the uplighter may especially be used for indirect lighting, such as by lighting a ceiling and/or parts of the wall.

Hence, indirectly the uplighter may also contribute to the illumination of a surface that also receives light from the downlighter. Instead of the terms "uplighting" or "uplighter", and similar terms, also the terms "indirect lighting" or "indirect lighter" (or light source for generating indirect light), respectively, or similar terms may be used; see further also below.

In other specific embodiments, the first light source light has a first optical axis, the second light source light has a second optical axis, wherein the first light source and the second light source are configured to provide the first light source light and the second light source light with the optical axes having a mutual angle $\alpha 1 = 0°$. In such embodiments, the light sources per se may differ, especially in the sense that the angular distributions of the respective light sources relative to the respective light sources, is different. Hence, in such embodiments especially the beam shape may differ (as the optical axes are collinear). For instance, this may be the case when one of the first light source and the second light source is configured to generate light source light having a batwing type of light distribution, and the other of the first light source and the second light source is configured to generate light source light having a Lambertian type of light distribution.

Hence, the angular distributions of the light with respect to the lighting system may especially be different. They can be different in a plurality of ways (mean direction, spread of directions or beam width, or maybe even asymmetric versus symmetric distributions). In this way, they produce different illuminance values on planes with a different orientation.

In view of tolerances, "$\alpha 1 \neq 0°$" may also be interpreted as $\alpha 1$ is not selected from the range of $0-5°$ and "$\alpha 1 = 0°$" may be interpreted as $\alpha 1$ selected from the range of $0-5°$.

As already indicated (or implied) above, a surface receiving illumination of the first light source may also receive illumination from the second light source and/or another surface receiving illumination of the second light source may also receive illumination from the first light source. Hence, a surface may receive directly first light source light and optionally also indirectly first light source light, and such surface may receive directly second light source light and optionally also indirectly second light source light. For instance, in the case of the above-mentioned lighting system comprising an uplighter and downlighter, a horizontal plane below the lighting system may receive light of the downlighter and indirect light of the uplighter. A vertical plane, however, may receive indirect light of the uplighter and some indirect light of the downlighter. Hence, not only the direct light path may be considered to count for the illuminance value(s), but also (in embodiments) the indirect light.

The above indicated negative proportional dependence between the radiant flux of the first light source and the radiant flux of the second light source may thus be based on e.g. estimated application conditions, such as an average office room, an average open-plan office, an average hospital room, an average living room, an average bedroom, an average meeting room, etc. etc. As desirable, or compulsory, general lighting conditions for such rooms are known (to a person skilled in the art), and estimate can be made of the illuminances at different positions, such as a vertical plane (vertical illuminance), or a horizontal plane (such as below the lighting system)(horizontal illuminance). Hence, the negative proportional dependence may be chosen or preset (during or essentially right after production) based on a predefined relation between application related parameter and the negative proportional dependence (or during installation or refurbishment). The application related parameter may be defined on the basis of one or more of (a) dimensions of space wherein the lighting system is applied, (b) a reflectivity of elements in the space wherein the lighting system is applied, and (c) a type of activities applied in the space.

For instance, when the size of the space is relatively large, the impact of indirect light through reflections off the walls may be smaller than when the size of the space is relatively small.

The reflectivity of elements in the space may e.g. refer to the reflectivity of walls, the ceiling, furniture, and the floor (including e.g. a carpet) (and their impact (on the illuminances)). Though they may vary, especially in domestic or some hospitality appliances (e.g. hotels), for different type of applications realistic average values may be chosen. For instance, for hospital rooms, the negative proportional dependence may differ between rooms, between rooms in different departments of the hospital, between rooms of different hospitals, but an average value may work well in many of those rooms. Even, an average value may work relatively well in all type of rooms. Instead of the term "average value", also the term "function" or "average function" may be applied, as the value of the negative proportional dependence may e.g. depend upon the type of space, but also on the type and power of the light sources. The latter is of course known to the builder of the lighting system, or more especially the luminaire. Hence, the negative proportional dependence may be based on an assumption of the reflectivity of the elements (and their impact).

The type of activities applied in the space may refer (also) to e.g. the distinction between a living room, a bedroom, an office room, a meeting room, etc. etc. For instance, such activities may be indicative of average sizes, average reflectivities of elements, availability of other elements and their average reflectivities and orientations, like desks, chairs, beds, etc. etc.

Hence, the negative proportional dependence may be chosen or preset (during or essentially right after production) based on a predefined relation between application related parameter and the negative proportional dependence.

Alternatively, in embodiments the negative proportional dependence may be chosen on location. For instance, illuminances at one or more positions at one or more radiant fluxes of the first light source and the second light source may be measured with a light sensor, on the basis of which the control system may determine the negative proportional dependence based on a predefined relation between the light sensor signal (and the negative proportional dependence). Therefore, in embodiments the control system may further be configured to receive during a calibration procedure a light sensor signal, and to control in the controlling mode the first light source and the second light source in dependence of a predefined relation between the light sensor signal and the negative proportional dependence.

Alternatively or additionally, the control system may be configured to execute a procedure ("iteration process") wherein a user can define preferred settings. For instance, the control system may sequentially propose different ratios of radiant fluxes and the user (i.e. including an installer of the lighting system) can, based on e.g. personal exposure to the lighting system light in the space adapt the ratio. For instance, in a first stage a user can be offered a first ratio of the radiant fluxes. In a second stage, the person can subject himself or herself in the space to the lighting system light at one or more locations and define via an App or with a balance controller (like a knob, a touch key, or other sensor to receive instructions from a user) the desirable ratio. This ratio is at least temporarily stored by the control system. In embodiments, the first stage and second stage may be repeated at two or more different first ratios, which may lead to different desirable ratios. On the basis of the (one or more) desirable ratio(s) of the radiant fluxes, the control system can determine on the basis of a predefined relation between desirable ratios and the negative proportional dependence, the negative proportional dependence for the system (as configured in that space).

One or more of the above-indicated methods to arrive at the negative proportional dependence may be combined, such as factory settings which may be fine-tuned at location.

The term "predefined relation" especially refers to a database, which may be comprised by the control system, or to which the control system may have (remote) access, and wherein the relation between two parameters is indicated, such as in the form of a function or especially in the form of a table.

In this way or in these ways, it may be possible to (effectively) control illuminances in a space. In this way, it may thus also be possible to change a radiant flux of one of the light sources, while maintaining a desired illuminance (as the radiant flux of the other light source may be controlled via the (predefined) negative proportional dependence). Also, in this way or in these ways, it is possible to determine $c_1$. Therefore, on the basis of the (variable) radiant fluxes and on the basis of estimates, measurements, or an iteration process, $c_1$ can be determined. Effectively illuminances may be controlled in this way.

Especially, the horizontal illuminance can be defined at a point or as an average value over an area (usually calculated as the average of a grid of point values). Relevant horizontal illuminance values in office lighting are typically the average value on a desk or at the complete horizontal plane at desk height (when desk positions are not known). Desk height is typically about 0.75-0.85 m. In other applications, for example corridor lighting, the horizontal illuminance may be defined at the floor level. For such application the height could be 0 m. The vertical illuminance may in embodiments be measured at walls (sometimes the average over complete wall area, sometimes only a band at eye height). Hence, in such embodiments the height of measuring can be 0 m up to the full height of the room, or e.g. a band of, at e.g. a height range of 0.5-2 m. In other applications, like in warehouses or in shops, a vertical illuminance is defined at the position of a rack or a cabinet, wherever goods may be stored, over the full height of the rack. In another application, the vertical illuminance may be defined at eye level, for a sitting person (about 1.2 m above floor) or, less often, a standing person (about 1.8 m above floor).

Hence, in embodiments, the horizontal illuminance is defined as the illuminance at a horizontal surface at a first height (H1) over a floor or bottom selected from the range of 0.0-1.0 m, and the vertical illuminance is defined as the illuminance at a vertical surface, at a second height (H2) over the floor or bottom selected from the range of 0.0-2.5 m. The vertical illuminance may especially be determined at a second horizontal distance from the first light source and the second light source selected from the range of 0.5-5 m, such as 1-4 m. For instance, this distance may be selected from the reference point (see also above). Further, the vertical illuminance may especially be determined at a second height over the floor or bottom selected from the range of 0.0-2.5 m, such as at a height selected from the range of 0.5-2 m, such as at 1.2 m.

The term "space" may for instance relate to a (part of) hospitality area, such as a restaurant, a hotel, a clinic, or a hospital, etc. The term "space" may also relate to (a part of) an office, a department store, a warehouse, a cinema, a church, a theatre, a library, etc. However, the term "space" also relate to (a part of) a working space in a vehicle, such as a cabin of a truck, a cabin of an air plane, a cabin of a vessel (ship), a cabin of a car, a cabin of a crane, a cabin of an engineering vehicle like a tractor, etc. The term "space" may also relate to (a part of) a working space, such as an office, a (production) plant, a power plant (like a nuclear power plant, a gas power plant, a coal power plant, etc.), etc. For instance, the term "space" may also relate to a control room, a security room, etc. The term space especially relates to a space defined by a wall, a ceiling or roof, and a floor or bottom.

Above, the terms "horizontal illuminance" and "vertical illuminance" were already applied. Especially, the term "illuminance" is the amount of light striking a surface—also known as incident light, where the "incident" is the beam of light actually landing on the surface. Illuminance may be calculated as the density of lumens per unit area lux (lumens/square meter). Illuminance may e.g. be measured using a light meter, as is known to a person skilled in the art. Horizontal illuminance describes the amount of light landing on a horizontal surface, such as a desk, or the floor, and vertical illuminance describes the illuminance landing on a vertical surface, such as a wall. Another example of an illuminance is the ceiling illuminance (see also elsewhere).

Specifically, the first light source is configured to generate the first light source light providing one or more of a first horizontal illuminance $E_{h1}$ and first vertical illuminance $E_{v1}$, wherein the second light source is configured to generate the second light source light providing one or more of a second horizontal illuminance $E_{h2}$ and second vertical illuminance $E_{v2}$. Note that these illuminances may be provided by direct light source light of the first light source and/or the second light source and/or may be provided by indirect light source light of the first light source and/or the second light source. Hence, the first light source is configured to generate the first light source light providing the first horizontal illuminance $E_{v2}$ and the first vertical illuminance $E_{v1}$, and the second light source is configured to generate the second light source light providing the second horizontal illuminance $E_{h2}$ and the second vertical illuminance $E_{v2}$, wherein $E_{h1} > E_{h2}$, and wherein $E_{v2} > E_{v1}$, at least when both the first and second light source are operated at the same, equal power. Of course it could occur that when the first light source and the second light source are operated at significantly different powers or that one type of the light sources is turned off while the other type of the light sources is still in operation, that $E_{h1} > E_{h2}$ and $E_{v1} > E_{v2}$ or that $E_{h2} > E_{h1}$ and $E_{v2} > E_{v1}$. However, typically the lighting system is configured such that when the first and second light sources(s) are each operated at equal power, which could be at their respective nominal power, that $E_{h1} > E_{h2}$ and $E_{v2} > E_{v1}$. In other words, in the lighting system the first light source is configured, for example by its orientation or by being provided with first respective, specific light redirection optical means like a first reflector, light guide or lens, to provide more horizontal illuminance than vertical illuminance, while the second light source is configured to provide more vertical illuminance than horizontal illuminance by being provided with second respective, specific light redirection optical means like a second reflector, light guide or lens.

In embodiments, $E_{h1} > E_{h2}$. Further, in embodiments $E_{v2} > E_{v1}$. In other words, in embodiments the first light source may more strongly contribute to the horizontal illuminance, such as a downlighter and the second light source may more strongly contribute to the vertical illuminance.

As indicated above, in a controlling mode over at least part of one of the first dimming range and the second dimming range, a sum of the horizontal illuminances or a sum of the vertical illuminances may be kept constant.

As indicated above, the light sources may essentially be the same, such as solid state light sources of the same bin (which may slightly vary within the bin, but which are considered essentially the same). Therefore, in specific embodiments the first light source light has a first spectral composition, and the second light source light has a second spectral composition identical to the first spectral composition. Here, identical may e.g. refer to essentially the same spectral distribution, leading to essentially the same color point, and essentially the same color rendering of different colors (such as essentially the same R1-R8 values, or even the same R1-R15 values).

In other embodiments, however, the first light source light has a first spectral composition, wherein the second light source light has a second spectral composition, different from the first spectral composition. In such embodiments, especially both light sources may be configured to generate white light, but having different correlated color temperatures. In further specific embodiments, the correlated color temperature of the light source primarily providing horizontal illumination may be lower than the correlated color temperature of the light source primarily providing vertical illumination, such as at least 100 K lower, like at least 500 K lower, like at least 700 K lower. Hence, in specific embodiments the first light source and the second light source are both configured to provide white (first and second) light source light, but they may be different in one or more aspects selected from the group consisting of color point, CCT, color rendering, melanopic response, and any other alpha-opic response.

Irradiance, i.e. the radiant flux (in Watt) at a (virtual) surface, is determined in Watt/m$^2$. Illuminance is the luminous flux (in lumen) at a (virtual) surface, determined in lumens/m$^2$ (which is also indicated as lux). To change from watts to lumens, the photopic luminosity function or photopic sensitivity curve is applied. Hence, illuminance in lumens/m$^2$ may also be indicated as "photopic illuminance" (or "photopic irradiance"). Other spectral weight functions may also be applied, related to specific sensitivities (of different photoreceptors in the eye). Such sensitivity curves are indicated as α-opic sensitivity curves, which are amongst others described by Phillip H. Ewing et al., in "Simulating Circadian Light: Multi-Dimensional Illuminance Analysis", Proceedings of the 15$^{th}$ IBPSA Conference, San Francisco, CA, USA, August 7-9, 2017, (e.g. http://www.ibpsa.org/proceedings/BS2017/BS2017_660.pdf or https://www.researchgate.net/publication/3262,52 Simulating_Circadian_Light_Multi-Dimensional_Illuminance_Analysis) DOI: 10.26868/25,708.2017.660, which is herein incorporated by reference (especially FIG. 1 of this paper). Here, the symbol "α" represents any of the photoreceptors in the eye, like rods, any of the three cones, or the intrinsically photosensitive retinal ganglion cells (ipRGCs) or melanopsin containing photoreceptors that are linked to non-visual effects of light.

Strictly speaking, non-photopic "illuminances" should be referred to as "irradiances", though in practice, the term illuminance is often applied for photopic illuminance as well as for any other α-opic "illuminance".

Hence, when controlling an illuminance, it may be one or more of the photopic illuminance, a crythropic illuminance, a chloropic illuminance, a rhodopic illuminance, a melanopic illuminance, and a cyanopic illuminance. Hence, though above a photopic illuminance may be assumed when discussing illuminance, above embodiments related to illuminance(s) may also in other variants refer to one (or more) of the other illuminances.

Therefore, the lighting system is in embodiments configured to generate (in a controlling mode) lighting system light comprising one or more of the first light source light and the second light source light, wherein the lighting system is configured to provide in a space wherein the lighting system is configured to provide the lighting system light with a controllable first illuminance and a controllable second illuminance at spatially different positions in the space. Especially, in the controlling mode of the control system the control system is configured to control a value of one of the first illuminance and the second illuminance. Even more especially, in the controlling mode one of the first illuminance and the second illuminance is maintained constant and wherein another of the first illuminance and the second illuminance is dimmed. Dimming may be done by a user. Alternatively or additionally, dimming may be based on a sensor signal of a (light) sensor. Yet further, alternatively or additionally dimming may be based on a time schedule.

In specific embodiments, the first illuminance and the second illuminance are selected from the group consisting of photopic illuminance, cyanopic illuminance, chloropic illuminance, erytrhopic illuminance, rhodopic illuminance, and melanopic illuminance.

The fact that the illuminance(s) may be different at different positions in a space or be different in different spaces, does not imply that the illuminance per se may not effectively (via the radiant fluxes) be controlled.

The terms "first illuminance" and "second illuminance" especially refer to spatially different of illuminances, but may additionally also refer to different types of illuminances. Hence, in embodiments the illuminances may differ because they are at different positions (and/or have different orientations), but they may also (additionally (or alternatively) differ because of relating to different alpha-opic illuminances.

When a lot of indirect lighting is used, a ceiling may become too bright. Therefore, in embodiments a possible application could be to set the ceiling illuminance at a constant value (to keep a constant brightness impression of the space and avoid a too high brightness level) and vary the task lighting. In such embodiments, the ceiling may have a role similar to the wall illuminance (herein described in other embodiments. Hence, in embodiments the first illuminance or the second illuminance may be selected from the group consisting of ceiling illuminance and a wall illuminance. For instance, the first illuminance may be a ceiling illuminance and the second illuminance may be the illuminance on the eye (assumed, assessed, or estimated under specific conditions, like office application, etc.). In other embodiments, the first illuminance may be the horizontal illuminance at a height below the ceiling, such as below 2 m, such as at the floor, and the second illuminance may be the ceiling illuminance. Herein, with the term "horizontal illuminance", in general illuminances are implied which are not the ceiling illuminance, but e.g. the illuminance at the floor, at a desk, etc.

As indicated above, the lighting system may be configured to generate in a controlling mode lighting system light comprising one or more of the first light source light and the second light source light. Further, as indicated above the lighting system may further comprise a user interface or may be functionally coupled to a user interface. The user interface is especially functionally coupled to the control system. Especially, in embodiments the control system may be configured to receive via the user interface one or more of user instructions selected from the group consisting of: (i) a total power of the lighting system light, (ii) a power of the first light source light, (iii) a power of the second light source light, (iv) a balance between the power of the first light source light and the second light source light, (v) an application related parameter, wherein the control system is configured to control in the controlling mode the first light source and the second light source in dependence of a predefined relation between application related parameter and the negative proportional dependence, and wherein the application related parameter is defined on the basis of one or more of (a) dimensions of a space wherein the lighting system is applied, (b) a reflectivity of elements in the space wherein the lighting system is applied, and (c) a type of activities applied in the space. The reflectivity of elements in the space may in embodiments refer to an average reflectively, or reflectivity of walls, reflectivity of the ceiling, reflectivity of the floor, reflectivity of furniture, etc.

The term dimensions may refer to one or more of length, width, height, diameter (if applicable)), especially of a space.

Hence, in embodiments a lighting system is provided which allows e.g. constant illuminance dimming, i.e. dimming of one of the light sources while maintaining a constant illuminance.

Therefore, in an aspect the invention also provides the use of the lighting system as described herein for maintaining a first illuminance constant while varying a second illuminance, different from the first illuminance, wherein the first illuminance and the second illuminance are selected from the group consisting of horizontal illuminance and vertical illuminance. In embodiments, the first illuminance and the second illuminance of illuminance are selected from the group consisting of photopic illuminance, cyanopic illuminance, chloropic illuminance, erytrhopic illuminance, rhodopic illuminance, and melanopic illuminance. Hence, the horizontal illuminance and the vertical illuminance may e.g. be both photopic illuminances, but in other embodiments, e.g. one of them is a melanopic illuminance.

In specific embodiments, the first illuminance and the second illuminance may be determined within an angle of incidence on a relevant reference surface smaller than 90°, such as smaller than 60°. Hereby, effectively an angle dependent filter is applied. For instance, when sitting at a desk light in a horizontal direction may have more (undesirable) impact than light under larger angles with a horizontal. Also, for instance the light incident from above may have a higher weight than light incident from below when determining the vertical illuminance for biological light dose. As different angles may have different impacts, it may not only be possible to use a kind of cut-off angle dependent filter, but it may also be possible to weight the angles, whereby angles of incidence that are more relevant (for a specific purpose or effect (whether or not desired), may have a larger (or smaller) weight than other angles. Therefore, in embodiments one or more of the first illuminance and the second illuminance are evaluated in dependence of an angle of incidence on a relevant reference surface, such as smaller than 90°. Hence, in embodiments an angular filter for illuminance at the eye may be applied when evaluating an illuminance. Therefore, when evaluating in dependence of an angular filter may especially imply that the contribution of an incoming light ray is weighted with a weighting function that depends on incidence angle.

The control system may be configured to control the first illuminance and the second illuminance by controlling the first radiant flux and the second radiant flux. The first illuminance and the second illuminance may be illuminances at specific point (at surfaces), or at a specific surface, in a space wherein the lighting system is applied.

As the exact space and elements in the space may not be known in advance, the control may be based on data about average spaces or assumptions, which allow defining a predetermined relation between the value of the first radiation flux and of the second radiant flux, such that the desired first illuminance and second illuminance at a specific point (at a surface), or at a specific surface, may be obtained, at least over part of the dimming range of the first light source or of the second light source. Hence, the control system may be configured to control the first illuminance and the second illuminance by controlling the first radiant flux and the second radiant flux based on predefined settings based on assumptions related to the illuminances in spaces where the lighting system may be applied. In embodiments, it may also be possible that the lighting system, especially the control system, may offer a menu, wherein the user (including an installer), may choose out of a limited set of possible applications (small office room, large office room, small meeting room, large meeting room, sleeping room, hall, hotel reception desk, etc. etc.), on the basis of which choice the control system determines the relevant dependence.

Alternatively or additionally, the control system may be configured to control the first illuminance and the second illuminance by controlling the first radiant flux and the second radiant flux, on the basis of sensor signals indicative of illuminances in the space. This may be based on an installation procedure (in principle once), or this may be a feedback loop (in principle constantly or intermittently during use of the system).

Alternatively or additionally, the control system may be configured to execute a procedure ("iteration process") wherein a user can define preferred settings (see also above).

The lighting device may be part of or may be applied in e.g. office lighting systems, industry lighting systems, warehouse lighting systems, household application systems, shop lighting systems, home lighting systems, accent lighting systems, spot lighting systems, theater lighting systems, etc.

BRIEF DESCRIPTION OF THE DRAWINGS

Embodiments of the invention will now be described, by way of example only, with reference to the accompanying schematic drawings in which corresponding reference symbols indicate corresponding parts, and in which:

In FIG. 9a, $d_{L,CT}$, (upper curve) indicates the dimming level of the Lambertian at constant task and $d_{L,CB}$ (lower curve) indicates the dimming level of the Lambertian at constant (room) brightness; FIG. 9b shows the illuminance E (lux) under constant task conditions; FIG. 9c shows the illuminance (lux) at constant room brightness. $E_{V,CT}$ (lower curve in FIG. 9b) indicates the vertical illuminance at constant task; $E_{H,CT}$ (upper curve in FIG. 9b) indicates the horizontal illuminance at constant task; $E_{H,CB}$ (upper curve in FIG. 9c) indicates the horizontal illuminance at constant room brightness, and $E_{V,CB}$ (lower curve in FIG. 9c) indicates the vertical illuminance at constant room brightness;

Figure 1:
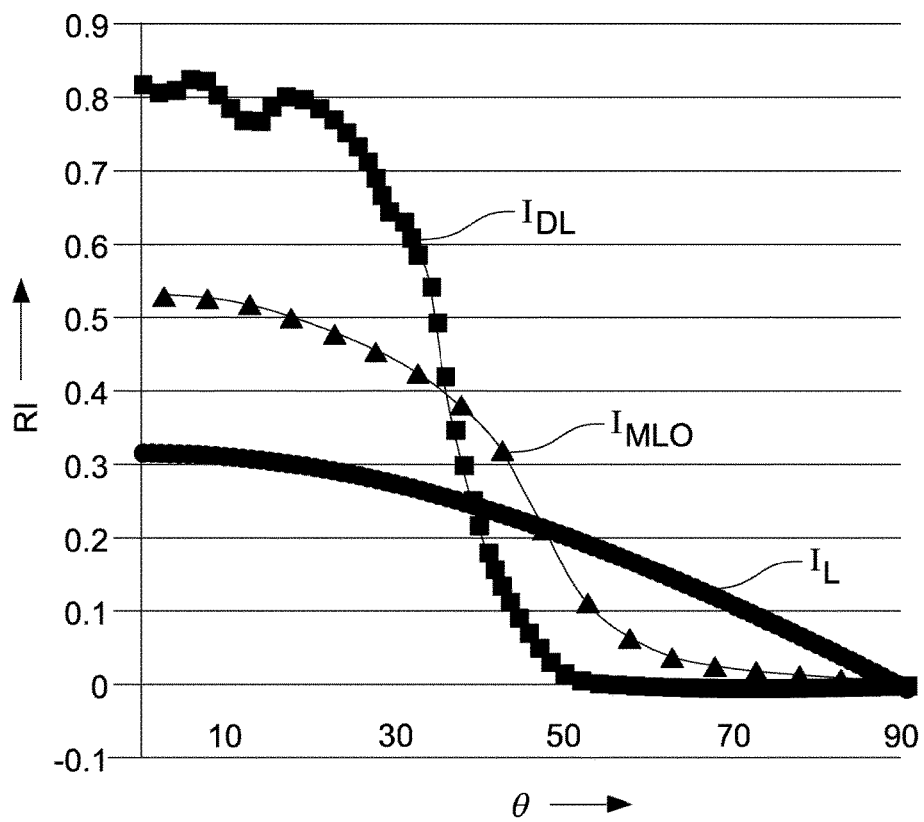
FIG. 1 depicts the relative intensity of a first light source, having a downlight light distribution, and has an intensity $I_{DL}$, and of a second light source, based on micro lens optics, $I_{MLO}$, as well as the relative intensity of a Lambertian $I_L$; on the x-axis, the angle θ relative to a normal to the lighting system in ° is indicated; on the y-axis the relative intensity (RI) in cd/lm; this first light source is also indicated as a downlighter and has a relatively narrow distribution (note that herein first light sources are not necessarily down lighters; this is just for the sake of the example chosen)

The schematic drawings are not necessarily to scale.

DETAILED DESCRIPTION OF THE EMBODIMENTS

Amongst others in embodiments herein a lighting system is proposed, especially with at least two separately dimmable beams, wherein in embodiments the two beams may have a different intensity profile (beam width, shape and/or direction) and/or wherein in embodiments the two beams may have a different spectrum. In this way, the two beams may in embodiments e.g. have different impacts on horizontal and vertical illuminance distributions in the room. For instance, the beams with a relatively strongest impact on horizontal illuminance may have a relative dim level H (between 0 and 1). The beams with a relatively strongest impact on vertical illuminance may have a dim level V (between 0 and 1). Instead of having the at least two channels (H, V) individually controllable, amongst others we propose embodiments wherein the two channels are simultaneously dimmed up and down, in embodiments e.g. according to a negative proportionality (V=V0−a*H), at least for a (significant) range of the dim levels. The proportionality constant "a" determines the mode at which the lighting system or luminaire is operated. For instance, in embodiments in a controlling mode one may vary a horizontal illuminance value while maintaining a certain vertical illuminance value. For instance, in other embodiments in a controlling mode one may vary a vertical illuminance level while maintaining a certain horizontal illuminance level. In the first mode, one can e.g. in embodiments dim the task lighting level without altering the room appearance or the EML value. In the second mode, one can e.g. in embodiments vary room appearance or biological light dose without altering the task illuminance (for instance, keep it at a fixed minimum level of 500 lux, as prescribed by European norm EN 12464-1 (2011). Further explanations, embodiments, and examples are provided below.

Herein, task illuminance especially refers to the illuminance on the (horizontal) task area (at the desk height), to distinguish it from other commonly used horizontal illuminances, such as surround illuminance (area immediately around the task area), background illuminance (area further away from the desks), floor illuminance, and ceiling illuminance. All these may play a role in lighting design and are described in EN12464-1. Hence, task illuminance may be defined as a horizontal illuminance at the task area, especially at "constant task lighting dimming". Hence, one may e.g. keep the task illuminance constant, while (up or down) dimming another illuminance.

We note that the vertical and horizontal illuminance values may be determined with different spectral weighting functions. Therefore, the spectral composition of the vertical illuminance and horizontal illuminance may be varied separately so that each of the five alpha-opic irradiances (see CEN/TR 16791:2017 "Quantifying irradiance for eye-mediated non-image-forming effects of light in humans") is set to a desired value that can be different for the horizontal and vertical exposures. This can be achieved with beams with an identical intensity distribution, but it may also be used with beams that are different in orientation or beam shape.

The value of the proportionality constant "a" for a certain mode may be determined by the maximum illuminance values that may be reached with the H and V channel and the fixed value that the user chooses (for either a horizontal or vertical illuminance value) (see also above). In embodiments, the fixed value may either be the starting value (user first dims H and V channels independently until a required value of illuminance is reached and then switches to the fixed value mode to vary the other illuminance value), or may be a numerical value input by the user. The maximum illuminance values of the H and V channel are either fixed in the controls, based on a typical use case, or are determined during a calibration step (measure the relevant illuminance values (especially without ambient light (daylight)) with first the H channel full on and V off, and then the V channel full on and H off), or are calibrated by using photo sensor input of all sensors in the lighting system or luminaire (again using typical room parameters or user input room parameters). The relevant illuminance values that may be to be controlled independently, may depend on the application.

A typical use case is, for instance, a large open-plan office. Other typical use cases are corridors, reception desk areas, small cell offices, industry halls, warehouses, shops, and etcetera.

For room controls, a relevant horizontal illuminance value may be the average horizontal illuminance at desk height (~0.75 cm above floor level, excluding the area within 0.5 m distance of the wall). The relevant vertical illuminance levels may also be room averages. Depending on the lighting quality metric to be kept constant, it can be average wall illuminance, average cylindrical illuminance at eye level of a sitting person (1.2 m above floor level). The averaging may be a simple weighted average of light coming from all directions, but it is also likely to be a vertical illuminance value that takes into account light from a restricted angular range, as we will argue below. This is all known to a person skilled in the art.

For the biological light dose, average vertical illuminance levels or average cylindrical illuminance levels at eye height may often be used. However, it is known that the field of view of a person is limited to about 50 degrees above the line of sight and about 70 degrees below the line of sight (limited by eyebrows and eyelids) under relatively dark lighting conditions. In bright spaces, people may start squinting and the field of view limits to +/−15 degrees with respect to the line of sight. In indoor spaces, the upper limit may likely be in between about 30 and 50 degrees above line of sight (see part of the angle β2 (above the horizon) in FIG. 10b). On average, the line of sight of a person working at a desk is assumed to be horizontal, or slightly downwards. Therefore, the relevant light dose for biological effects may especially be a vertical or cylindrical illuminance value with an upper angular limit between 30 and 50 degrees above horizon. The lower angular limit can be determined by the field of view (70 degrees below horizon), but it may also be at the horizon, because there are indications that the receptors for this light are less sensitive in the upper half of the retina.

Further, it seems that the room brightness perception may be dominated by luminance values at eye height at the horizon, within a 40 degrees band.

For individual controls, the horizontal illuminance may be considered the average illuminance value on the desk, or the value measured by a sensor on the desk. The vertical illuminance may be determined as a combination of wall and ceiling illuminances in the main viewing direction of a person sitting at the desk, or the vertical illuminance at eye level of a person sitting at the desk (possibly taking into account the limited field of view as discussed above).

It is noted that the intensity patterns (light beams) are not necessarily different in shape. A room with identical luminaires may be clustered as follows: one "H" luminaire right above the desk to be illuminated, and several "V" luminaires located near the walls. If the H luminaire is dimmed down to reduce the task light, the V luminaires may be dimmed up slightly to compensate for the drop in ambient light level caused by dimming down the H luminaire. In embodiments related to a single luminaire, rather than a lighting system, the beam directions or intensity patterns may especially be different.

In embodiments, at least two different lighting control channels may be dimmed with a negative proportionality. The channels may be different in the sense that they provide a different balance in horizontal versus vertical illuminance. The illuminance values may be local values (at the position of a desk or a specific observer) or an average over a certain area or space. The illuminance values may take into account all directions of incoming light (typically the case for horizontal illuminance values for task illumination), but they may also exclude light from certain directions (for instance to determine the illuminance on the eye that is relevant for the biological light dose, or to determine the brightness of a space). The illuminance values may be determined with various spectral weighting functions, depending on the application: for instance, photopic, scotopic or melanopic weighting functions may be used.

The most straightforward way to characterize balance between horizontal and vertical illuminance is the modelling index:

$$MI = E_v / E_h$$

where $E_v$ is the vertical illuminance (or cylindrical illuminance, if averaged over all orientations in the horizontal plane) and $E_h$ is the horizontal illuminance. The modelling index may be determined directly from the intensity distribution $I(\varphi, \theta)$, as provided in the photometric data for any luminaire:

$$E_h = \iint I(\varphi, \theta) \sin \theta \, d\varphi \, d\theta$$

$$E_v = \iint I(\varphi, \theta) \sin \theta \cos \varphi \tan \theta \, d\varphi \, d\theta$$

These are the integrated illuminance values provided by the direct light only, integrated over all emission directions with a downward component (positive cos θ value) in case of the horizontal illuminance and integrated over all directions with a component in the φ=0 direction (positive cos φ value) in case of the vertical illuminance (we will take into account the contributions of light reflections by walls and floors later on). In case of a rotationally symmetric beam I(θ), a very large space, and no limitations on incoming directions, these equations simplify to:

$$E_h = 2\pi \int_0^{\pi/2} I(\varphi, \theta) \sin \theta \, d\theta$$

$$E_v = 2 \int_0^{\pi/2} I(\varphi, \theta) \sin \theta \tan \theta \, d\theta$$

In the FIG. 1, we show three different intensity profiles: a beam with a very sharp intensity cutoff, typical for high performance down lighters ("DL"), a beam with a soft cutoff, typical for low glare recessed fixtures ("MLO", i.e. micro lens optical plate), and a Lambertian distribution (constant luminance, typical for diffuse light sources like troffers with a diffuse exit, or indirect lighting).

The modelling index for these three beams is:

| Direct light only | DL | MLO | Lambertian |
| --- | --- | --- | --- |
| MI (all directions) | 0.17 | 0.26 | 0.50 |
| MI (Ev only 45-90°) | 0.022 | 0.13 | 0.40 |

This table describes the Modelling indices for three types of light beams, neglecting light recycling by reflective surfaces in a space. The Modelling index is calculated conventionally (taking into account all directions of incident light) and by excluding directions that have almost no biological impact.

Here, we calculated the Ev either for all directions of incoming light (first row) or for only the light within 45 and 90 degrees to the vertical direction (second row).

In a real space, the reflections by walls, floor, objects, and ceiling add an indirect illuminance component to both the horizontal and the vertical illuminance values. We recalculated the modelling index (with and without directional screening) for a room of 7.2 m by 14 m and 2.7 m height. The ceiling reflectance is 70%, the wall reflectance 50% and the floor reflectance 20%. All room surfaces are Lambertian scattering. The horizontal illuminance is calculated at desk level (0.75 m height) and the vertical (cylindrical) illuminance at eye height of a sitting person (1.2 m height).

| Direct & indirect light | DL | MLO | Lambertian |
| --- | --- | --- | --- |
| MI (all directions) | 0.32 | 0.42 | 0.60 |
| MI (Ev only 45-90°) | 0.094 | 0.19 | 0.40 |

This table describes Modelling indices for three types of light beams, taking into account light recycling by reflective surfaces in a space. The Modelling index is calculated conventionally (taking into account all directions of incident light), and by excluding directions that have almost no biological impact. We note that all modelling indices increase by the additional diffuse background light, originating from room surface reflections. Furthermore, the differences between the different light sources are reduced by the room reflections. We note that the impact on the screened MI is much less. In smaller rooms, and/or in rooms with higher surface reflectivity values, the impact of room reflections on MI will be higher.

Figure 2:
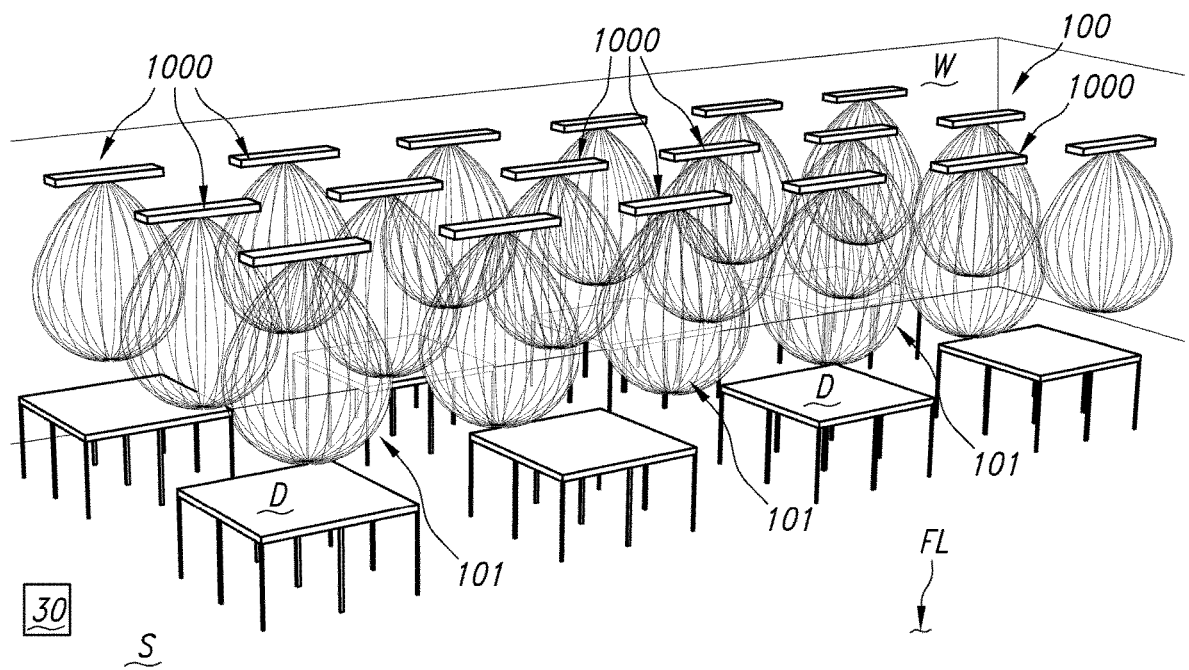
FIG. 2 schematically depicts a possible arrangement of lighting systems, or a lighting system with a plurality of modules or luminaires.

FIG. 2 schematically depicts a space S with walls W and a floor FL. The ceiling is not depicted in this schematic drawing. Reference D refers to a desk (surface). Schematically, a lighting system 100 is depicted. Here, the lighting system 100 comprises a plurality of modules 1000. The modules 1000 provide light. The light provided by the lighting system 100 (here from the modules) is indicated as lighting system light 101.

The lighting system 100 comprises a first light source, a second light source, and a control system 30. In embodiments, at least one of the luminaires 1000 comprises the firsts light source 10 and the second light source 20. A luminaire 1000 may also comprise a plurality of the first light sources 10 and a plurality of the second light sources 20.

The first light source (not separately visible) is configured to generate first light source light with a controllable first radiant flux. The first radiant flux is dimmable over a first dimming range.

The second light source is configured to generate second light source light with a controllable second radiant flux. The second radiant flux is dimmable over a second dimming range.

The lighting system light comprises first light source light and/or second light source light. A single module may comprise both types of light sources and/or first modules may comprise only (or mainly) first light sources) and second modules may comprise only (or mainly) second light sources.

As the first light source(s) and the second light source(s) have different angular distributions (see below) relative to the lighting system, at different spatial position in the space S, different illuminances may be experienced (even at identical distances from the lighting system (or from the modules).

The control system 30 is configured to control the first light source and the second light source. In a controlling mode of the control system 30, the control system 30 is configured to control a value of one of the first radiant flux and the second radiant flux with a negative proportional dependence of a change in a value of the other of the first radiant flux and the second radiant flux over at least a respective part of the respective dimming range. Hence, in this controlling mode the lighting system light will in general comprise both the first light source light and the second light source light.

In this way, e.g. the wall illuminance may be kept constant over part of the dimming range of another illuminance, such as at the floor FL or at the desk(s) D. Or, e.g. the ceiling illuminance may be kept constant over part of the dimming range of the illuminance at the floor FL or at the desk(s) D. Or, e.g. the wall illuminance may be kept constant over part of the dimming range of the illuminance at the floor FL or at the desk(s) D. Other options may also be possible.

Figure 3:
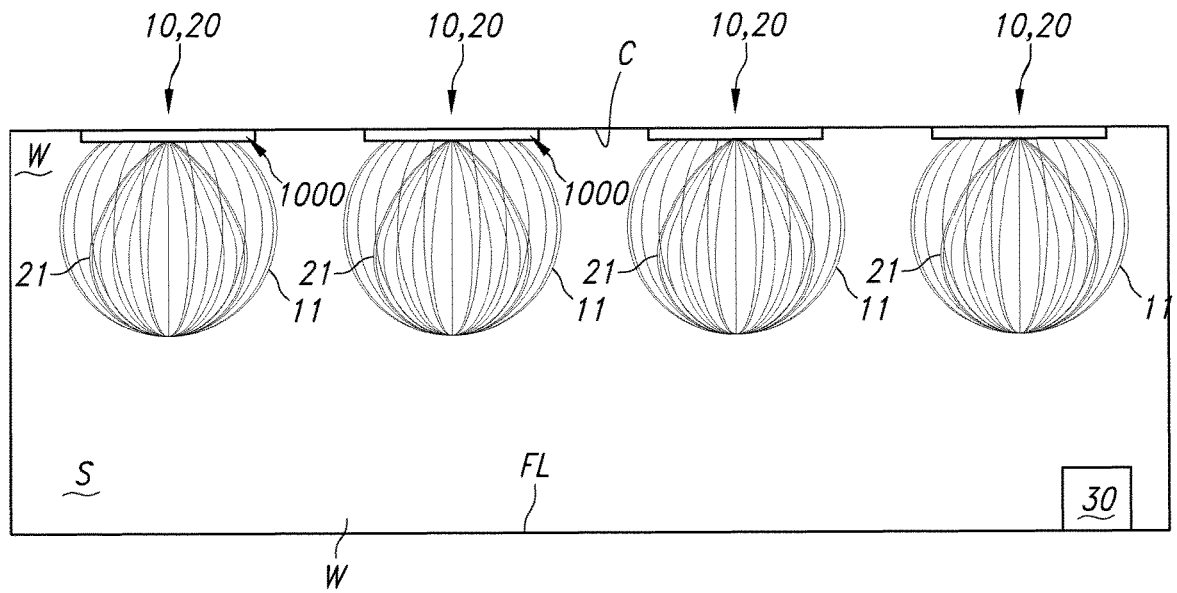
FIG. 3 schematically depicts such lighting system(s) or modules in a cross-sectional view, also showing two different angular distributions of the first light source light and the second light source light.

Below, an embodiment is further described, of a room with recessed downlights (intensity cut-off beam) and diffuse troffers. In this embodiment, the luminaire is capable of emitting light with a broad intensity distribution, and light with a good cut-off at high angles. In the example below, we take a Lambertian beam and an intensity profile of a downlight lamp herein also indicated with reference "DL". FIG. 3 shows a cross-section of a room simulated in Dialux, a lighting design software package.

Here, an embodiment is shown wherein each luminaire 1000 comprises one or more first light sources 10 and one or more second light sources 20. The one or more first light sources 10 are configured to generate first light source light 11. The one or more second light sources are configured to generate second light source light 21. The angular distribution of the first light source light 11 and the second light source light 21 are shown in overlay. The first light source light 11 has an essentially Lambertian distribution, see also FIG. 1; the second light source light 21 has a light distribution as indicated with $I_{DL}$ in FIG. 1.

As shown, the first light source light 11 has a first angular distribution relative to the lighting system 100. Further, the second light source light 21 has a second angular distribution relative to the lighting system 100, different from the first angular distribution.

Hence, in embodiments the first light source light 11 may have a first angular distribution relative to the luminaire 1000, and the second light source light 21 may have a second angular distribution relative to the luminaire 1000, different from the first angular distribution.

Reference C indicates the ceiling.

At maximum output, the Lambertian beams provide a horizontal illuminance $E_{h,L,max}$ and the DL downlights produce a horizontal illuminance $E_{h,DL,max}$. The horizontal illuminance values then follow from $$E_{h,L} = d_L E_{h,L,max}$$

$$E_{h,DL} = d_{DL} E_{h,DL,max}$$

where $0 < d_L < 1$ and $0 < d_{DL} < 1$ are the relative dimming levels of the Lambertian and DL lighting channel.

The vertical illuminance is a measure for the brightness of vertical planes in the space (walls, columns, people, and etcetera). The contributions to the vertical illuminance follows from $$E_{v,L} = MI_L E_{h,L}$$

$$E_{v,DL} = MI_{DL} E_{h,DL}$$

where $MI_L$ and $MI_{DL}$ are the modelling indices of the Lambertian and DL sources. We take the values of table 2 (taking into account room surface reflections in a large office space). We assume both maximum horizontal illuminance values are 500 lux (adding up to 1000 lux if both channels are full on).

Below, we will illustrate two different dimming scenarios according to the invention:

Dimming the room brightness while keeping a constant task lighting $E_h$

The relation between the two dimming levels is given by $$d_L = (E_h - d_{DL} E_{h,DL,max}) / E_{h,L,max}$$

Dimming the task lighting while keeping a constant "room brightness" $E_v$

The relation between the two dimming levels is given by $$d_L = (E_v - d_{DL} E_{v,DL,max}) / E_{v,L,max} = (E_v - d_{DL} MI_{DL} E_{h,DL,max}) / (MI_L E_{h,L,max})$$

Figure 4:
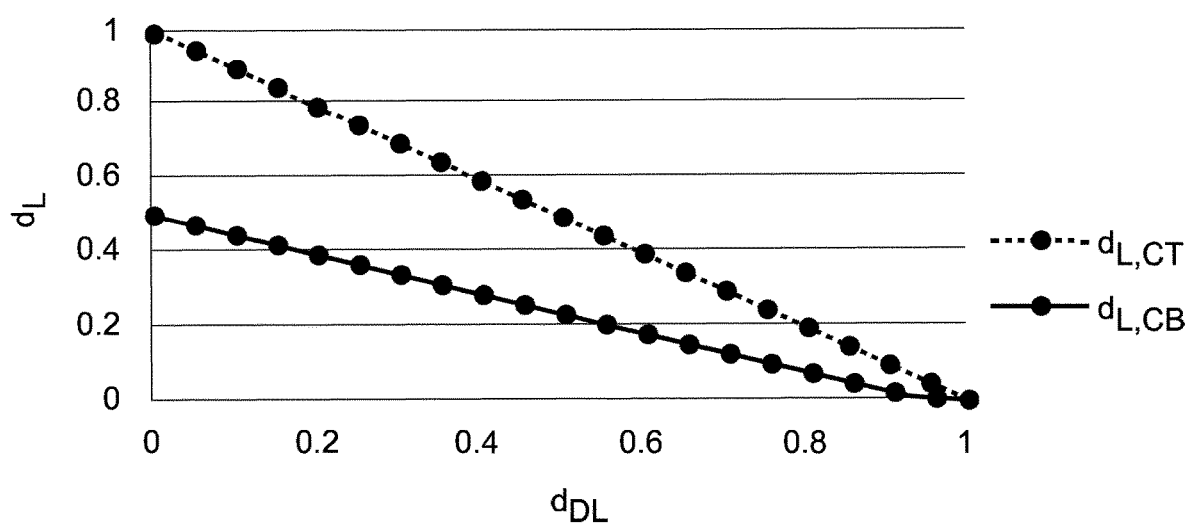
FIG. 4 depicts the dimming levels, with on the x-axis $d_{DL}$ (dimming factor of the first light source with a downlight intensity distribution) and on the y-axis $d_L$ (dimming factor of the second light source with Lambertian intensity distribution), wherein the curve $d_{L,CT}$ indicate constant task lighting and the curve $d_{L,CB}$ indicates constant (room) brightness). Note that at CB the value of $d_L$ can vary essentially only between 0 and 0.5. Actually, the horizontal and vertical axes may be interchanged: $d_L$ and $d_{DL}$ are linearly dependent in an equal way. Hence, one may also plot the (linear) relation the other way around.

The relations between Lambertian and DL dimming levels are plotted in FIG. 4 for the constant task illuminance scenario and for the constant room brightness scenario. Note that both show a negative proportionality, albeit with different slope.

Figure 5A:
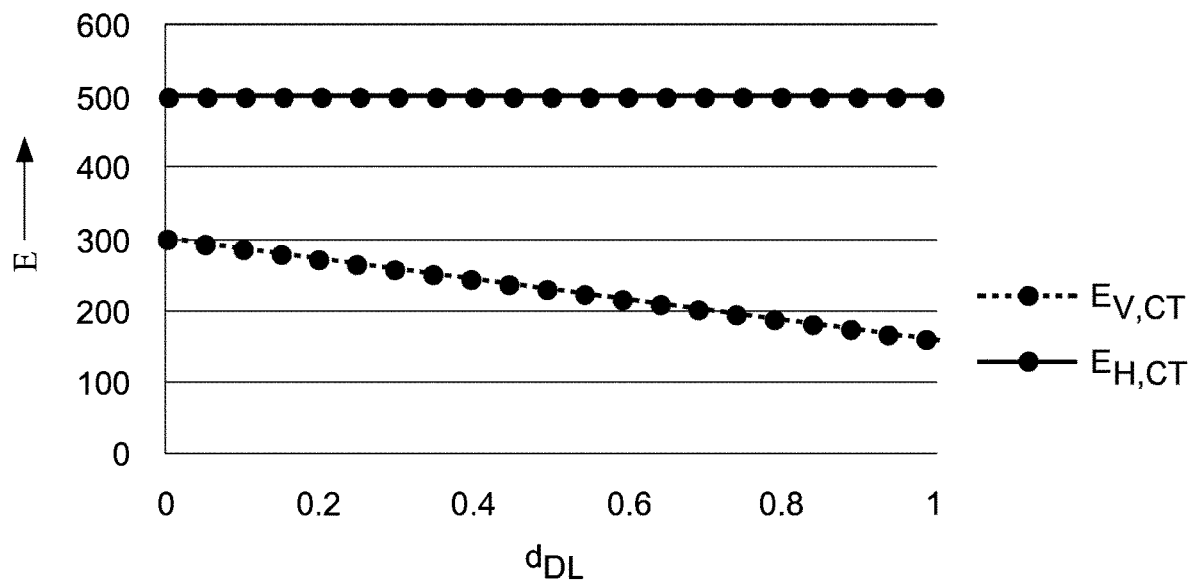
FIGS. 5a and 5b indicate the horizontal illuminance ($E_H$) (upper curves in FIGS. 5a and 5b) and vertical illuminances ($E_V$) (lower curves in FIGS. 5a and 5b) at constant task (CT) illumination (5a) or constant room brightness (CB) (5b); in the constant task lighting scenario, the horizontal illuminance is fixed at 500 lux, while the vertical illuminance varies from 160 to 300 lux. In the constant room brightness scenario, the vertical illuminance is fixed at 150 lux, while the horizontal illuminance varies between 250 lux and 500 lux; on the y-axis, the illuminances E in lux are indicated, on the x-axis $d_{DL}$ is indicated; $E_{V,CT}$ (lower curve in FIG. 5a) is a measure for the vertical illuminance (a measure for the perceived or room brightness) at constant task; $E_{H,CT}$ (upper curve in FIG. 5a) indicates e.g. the horizontal illuminance (a measure for the task illuminance) at constant task lighting; $E_{H,CB}$ (upper curve in FIG. 5b) indicates horizontal illuminance or task illuminance at constant (room) brightness, and $E_{V,CB}$ (lower curve FIG. 5b) indicates the vertical illuminance or wall illuminance, which is a measure for the room brightness, at constant room brightness.
Figure 5B:
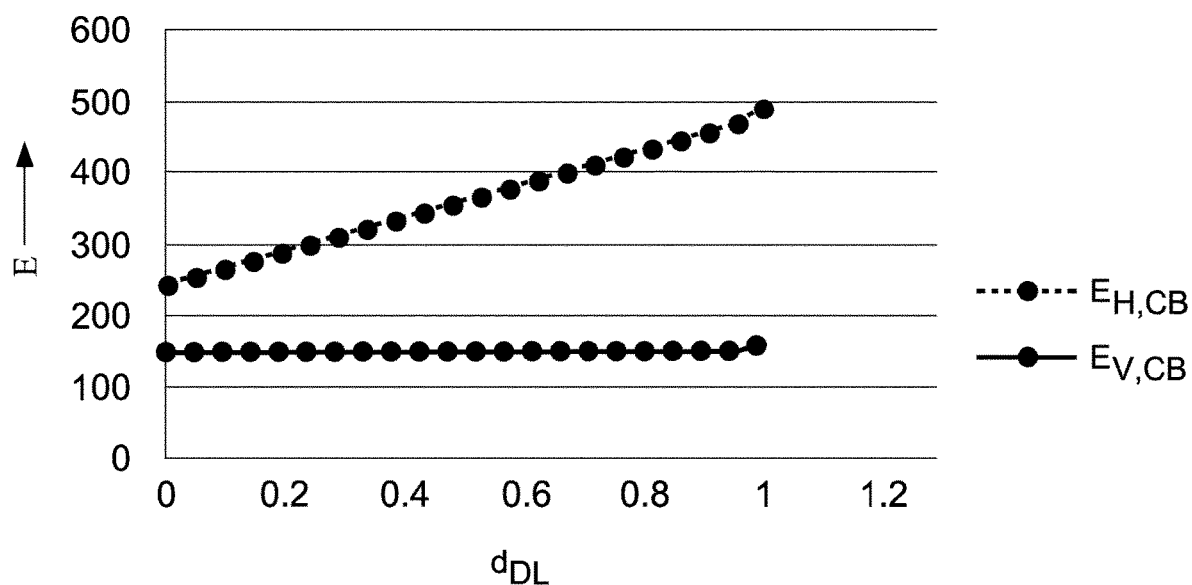

The horizontal and vertical illuminance values are shown in FIGS. 5a-5b. In the constant task lighting scenario, the horizontal illuminance is fixed at 500 lux, while the vertical illuminance varies from 160 to 300 lux. In the constant room brightness scenario, the vertical illuminance is fixed at 150 lux, while the horizontal illuminance varies between 250 lux and 500 lux. See also FIGS. 5*a*-5*b*.

Figure 6:
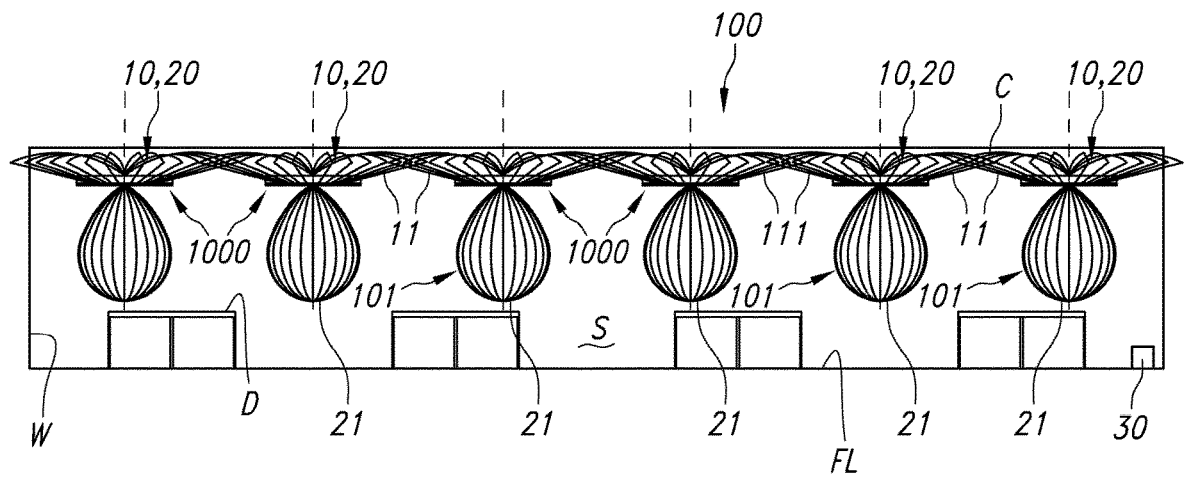
FIG. 6 schematically depicts a cross-sectional side view of an office space with an array of desks and an array of suspended luminaires. The suspended luminaires all have a direct light beam downward with the downlight intensity distribution, and an indirect light beam upward with a batwing-type distribution to provide an even illumination of the ceiling. The indirect lighting that is diffusely reflecting off the ceiling has a Lambertian intensity distribution (not drawn).

Below, an embodiment is further described, of suspended luminaires with constant biological light dose. In this embodiment, the room is lit by suspended luminaires. The direct lighting downward is with a sharply defined beam, similar to that of the DL downlight, whereas the indirect lighting via the ceiling is Lambertian. The room is the same as in the previous embodiment. Different than in the previous embodiment, we now want to vary the biological light dose (vertical illuminance with a limited range of incident light, see the modelling indices of table 2) and the horizontal task light. For simplicity, we ignore the impact of spectral weighing (in principle, the vertical illuminance should be weighed by a melanopic response curve, not the photopic response curve). See also FIG. 6. Here, the first light source 10 may be an uplighter, generating first light source light 11 directed to the ceiling C; the second light source 20 may be a downlighter, generating second light source light 21, directed to the floor FL (and also the walls W).

Figure 7:
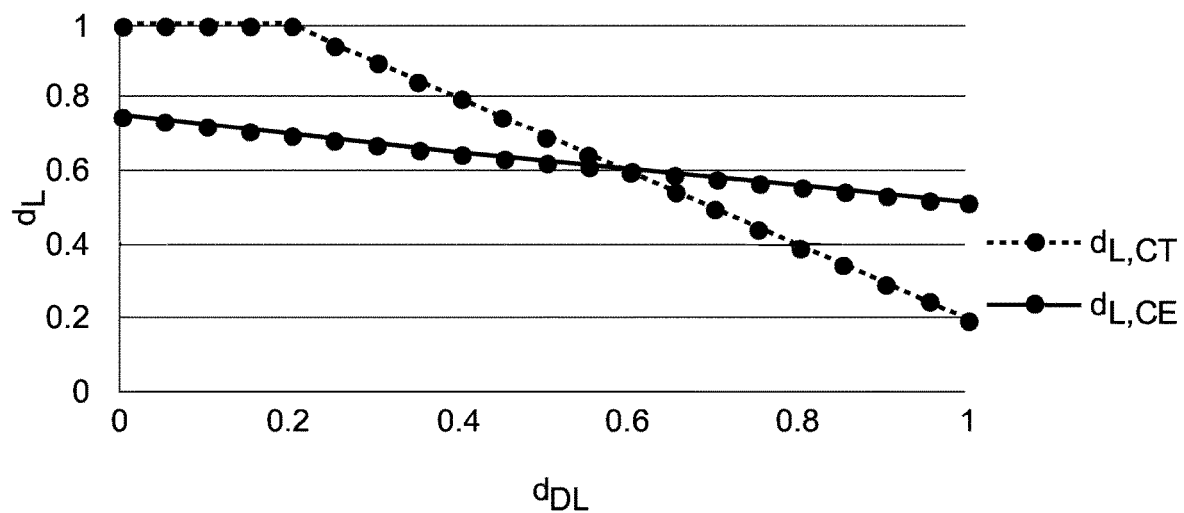
FIG. 7 shows the relation between dimming of a Lambertian type light source and the above indicated first light source with down lighting properties; the dimming levels are indicated for constant task lighting $d_L$ (for the Lambertian), i.e. $d_{L,CT}$, (curve starting at $d_L=1$ at $d_{DL}=0$) and dimming levels for the constant eye illuminance lighting $d_L$ (for the Lambertian), i.e. $d_{L,CE}$, (starting at $d_L=0.75$ at $d_{DL}=0$). CE indicates a constant eye illuminance (i.e. the illuminance at the eye is kept constant). It is the vertical illuminance at eye level, with an angular filter that blocks incoming light at large angles to the normal of the plane. This vertical illuminance value is taken as a measure for the biological light dose, i.e. the light dose that is responsible for non-visual effects. The proportionality is valid for a limited range of dimming values: at very low dim levels of the direct beam ($d_{DL}<0.2$), the set constant task level cannot be reached. Further, $d_L$ is even more limited in range for CE, about 0.5-0.75.

The relations between Lambertian and DL dimming levels are plotted in FIG. 7 for the constant task illuminance scenario and for the constant biological light dose scenario.

We note that the proportionality is valid for a limited range of dimming values: at very low dim levels of the direct beam ($d_L<0.2$), the set constant task level cannot be reached.

Figure 8A:
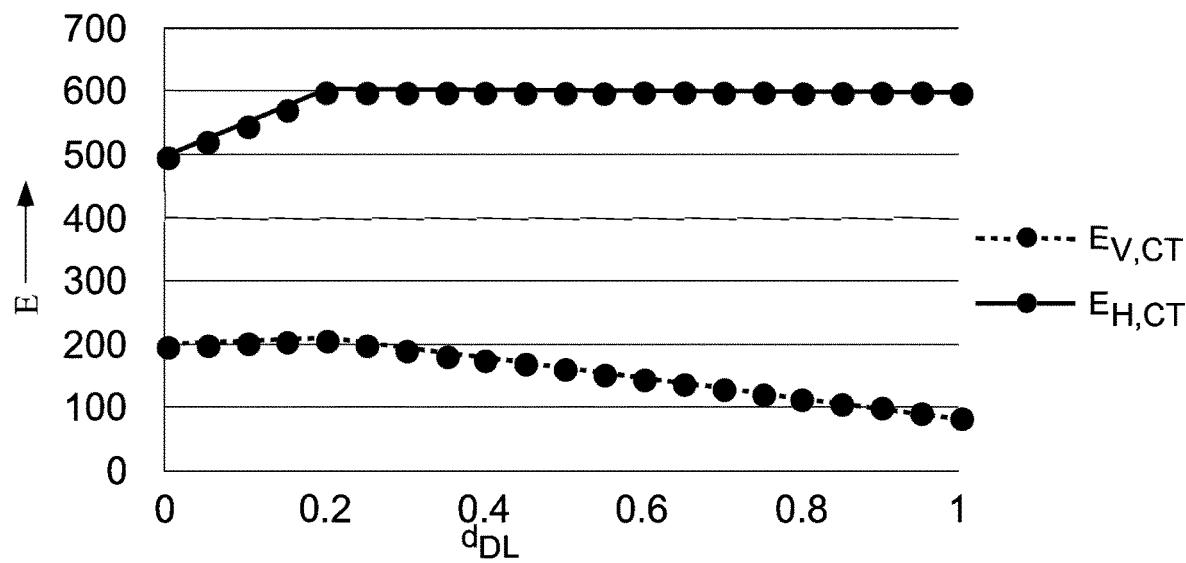
FIGS. 8a-8b show the horizontal (task) and vertical (eye) illuminances for the constant task lighting scenario (CT) (FIG. 8a) or the constant eye illuminance scenario (CE) (FIG. 8b), with on the x-axis $d_{DL}$, i.e. the dimming level over the first light source of the downlighter type, and on the y-axis the illuminance (lux). In the constant task lighting scenario, the horizontal desk illuminance is fixed at 600 lux, while the vertical eye illuminance varies from 87 to 209 lux. In the constant biological light dose scenario, the vertical eye illuminance is fixed at 150 lux, while the horizontal desk illuminance varies between 375 lux and 758 lux.
Figure 8B:
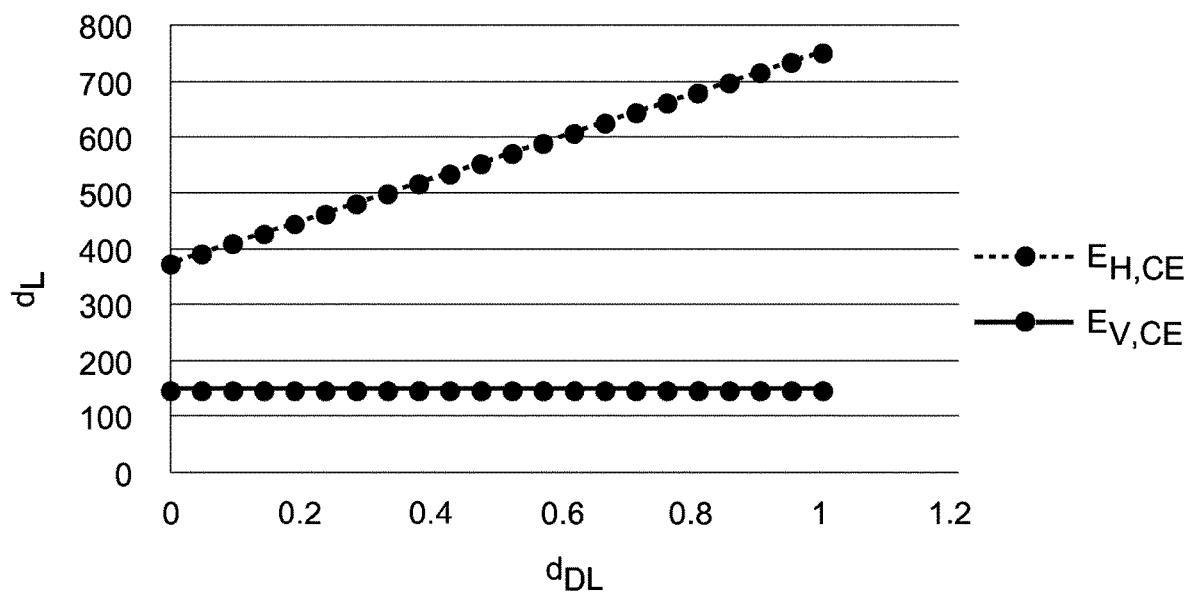

The horizontal illuminance and vertical illuminance (with limited range of incident light) values are shown in FIGS. 8*a*-8*b*. In the constant task lighting scenario, the horizontal illuminance is fixed at 600 lux, while the vertical illuminance varies from 87 to 209 lux. In the constant biological light dose scenario, the vertical illuminance is fixed at 150 lux, while the horizontal illuminance varies between 375 lux and 758 lux, see also FIGS. 8*a*-8*b*.

Below, an embodiment is further described, of suspended luminaires with direct MLO beams, indirect lighting, and constant wall illuminance. In the previous two embodiments, we have used lighting channels with a relatively large difference in modelling index (about a factor of 2 difference in embodiment 1 and about a factor of 4 difference in embodiment 2. In typical lighting systems, for instance a suspended luminaire, the direct light is MLO type and the indirect light is Lambertian after reflection off the ceiling. When we take into account room reflections, the modelling index is 0.42 for the direct light and 0.60 for the indirect light (different by a factor 1.4 only). For smaller rooms, like cell offices, the difference will be even less.

Figure 9A:
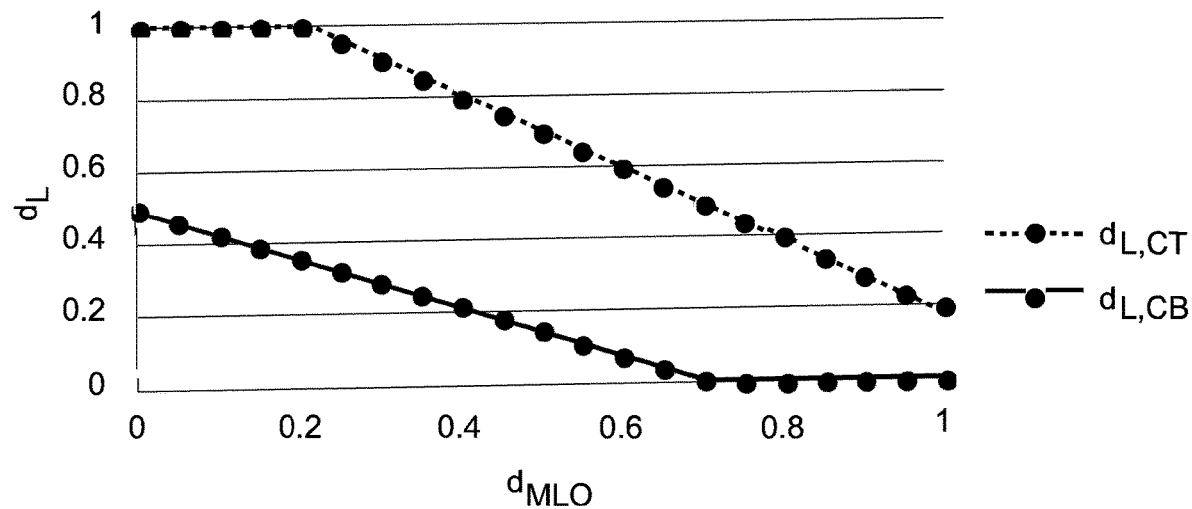
FIGS. 9a-9c show the dimming levels for the MLO type light source, with in FIG. 9a related to the dimming levels & of the Lambertian light source (indirect lighting via a diffuse reflecting ceiling), and in FIGS. 9b-9c the illuminance (lux) as function of the dimming level $d_{MLO}$ of the MLO type light source.
Figure 9B:
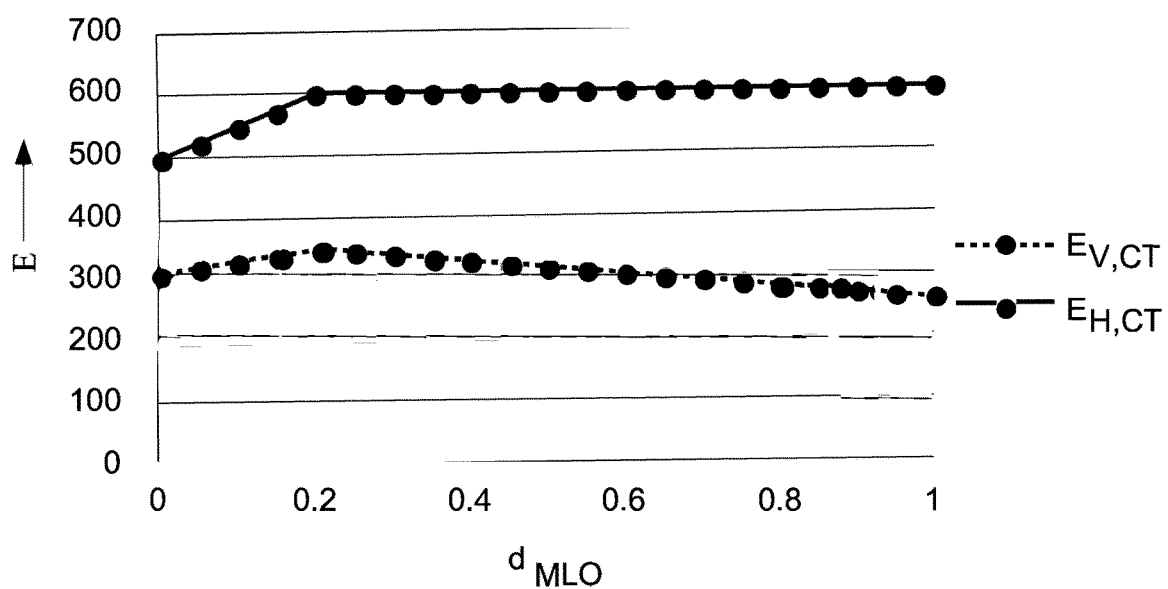
Figure 9C:
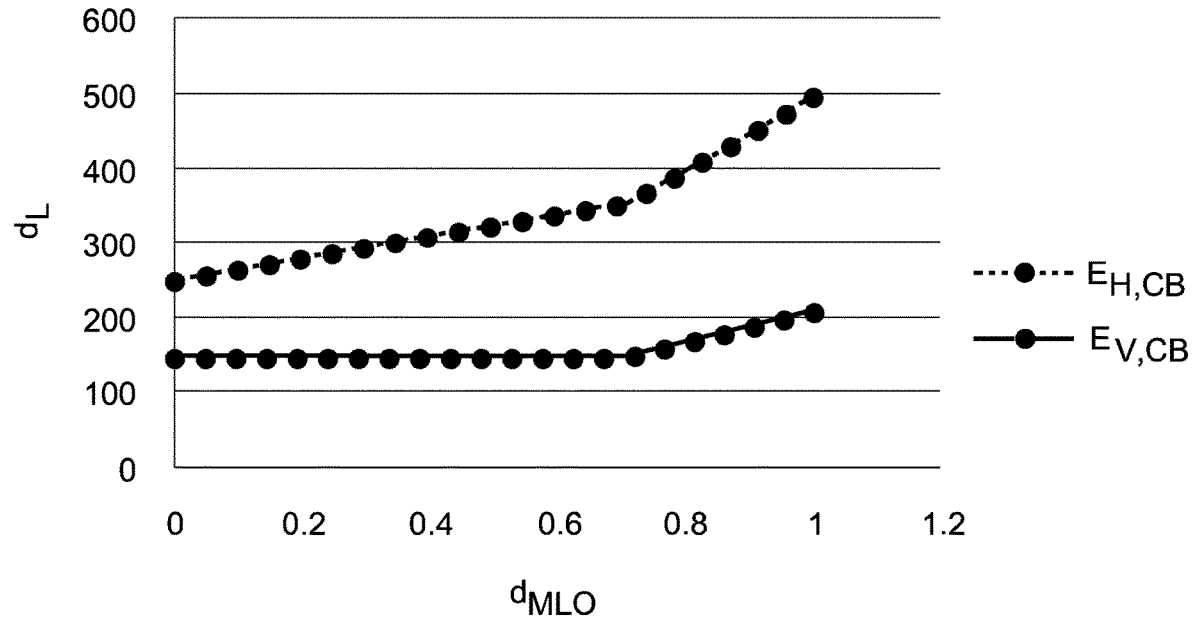

Fixing the constant task illuminance at 600 lux, and the constant vertical illuminance at 150 lux, the dimming levels of the MLO beam and the Lambertian beam are coupled as indicated in FIGS. 9*a*-9*c*. In this embodiment, the vertical illuminance varies between 270 and 342 lux (at constant horizontal illuminance of 600 lux). The task illuminance varies between 250 and 355 lux at a constant vertical illuminance of value of 150 lux. We note that in this embodiment the range of variation is very limited: the invention is best applied for systems with a large difference in modelling index.

Below, an embodiment is further described, of illuminance setting, sensors, controls and connectivity. A lighting system with at least two beams of different light distribution where the negative proportionality of the dim levels of the two beams can be adjusted by the installer or end-user so that the amount of horizontal illuminance level in a space or at a position in that space can be set according to individual preferences, without any changes in the vertical illuminance level (or vice versa). To set the correct balance between the channels, the maximum illuminance values (both horizontal and vertical, weighed with the relevant spectral and/or directional filter) need to be known. The most straightforward method is to measure these values on site, under the relevant ambient lighting conditions. If an on-site calibration is not possible, the values may also be estimated as follows. The direct light values follow directly from the photometric data (intensity profile and maximum flux). The contribution of ambient light (via reflections in the room or ambient light entering via windows) can be estimated, determined by simulation, or estimated on the basis of room size and room surface reflectance values. For instance, the MI values in table 2 (including room reflections) are higher than the values obtained from direct calculation in table 1. The table 2 MI values can be derived from the table 1 MI values by adding ~100 lux diffuse ambient light to both horizontal and vertical illuminance (calculated @500 lux total horizontal illuminance):

$$MI_{direct+indirect}=E_v/E_h=(E_{v,direct}+E_{ambient})/(E_{h,direct}+E_{ambient})=MI_{direct}(1-E_{ambient}/E_h)+E_{ambient}/E_h$$

The table 2 MI values can be derived from the table 1 MI values by adding ~100 lux diffuse ambient light to both horizontal and vertical illuminance (calculated @500 lux total horizontal illuminance). The MI values with directional filter can be calculated in a similar way, only different in the fact that the vertical illuminance contribution is diminished by the directional filter:

$$MI_{direct+indirect}=E_v/E_h=(E_{v,direct}+E_{v,ambient})/(E_{h,direct}+E_{h,ambient})=MI_{direct}(1-E_{h,ambient}/E_h)+E_{v,ambient}/E_h$$

The values of table 2 are approximately obtained by adding ~100 lux horizontal ambient illuminance, and ~40 lux vertical ambient illuminance (calculated @500 lux total horizontal illuminance).

These ambient light levels are for a relatively large room (7.2 m by 14.4 m, 2.7 m height), with default surface reflectance values (0.7, 0.5 and 0.2 ceiling, wall and floor reflectance) without daylight. For smaller rooms, rooms with higher reflectance values, or rooms with daylight, a higher ambient room illuminance should be added. This value can be an adjustment parameter in the controls, to be tuned by the user: the user sets the adjustment parameter such that the task light remains constant in constant task lighting mode, and that the vertical illuminance is constant in the other mode.

Another option is that the horizontal or vertical illuminance level is determined automatically based on sensor input. This sensor input may be local (from sensors in the luminaire), but the input may also come from separate sensors or other luminaires and communicated by wire or wirelessly. The sensor may be a photo sensor or a lux meter, and it may comprise a spectral filter or directional filter (shield) to modify the incoming light signal. This illuminance level at the sensor is then set without affecting the other illuminance level (for instance the vertical illuminance level if the sensor is measuring horizontal illuminance, and vice versa). The luminaire may be autonomous, or the setting may be determined for a group of luminaires in a zone, in a room, a floor, or a whole building.

Below, an embodiment is further described, of dynamic lighting. A dynamic lighting system that provides a lighting rhythm where the vertical illuminance or biological light dose can be controlled over time and/or location, without changing the task illuminance.

Below, an embodiment is further described, of a variable spectrum. Any from the above embodiments where the spectral composition of the light of the two beams is different (either in color, or in correlated color temperature). The beams may be identical in intensity distribution. Because of the different spectra, the melanopic light dose will be different for the two beams, and therefore also the modelling index will be different (if the melanopic weighing function is used only for the vertical illuminance). Therefore the biological light dose may be varied in such a system without changing the horizontal illuminance, or vice versa.

Figure 10A:
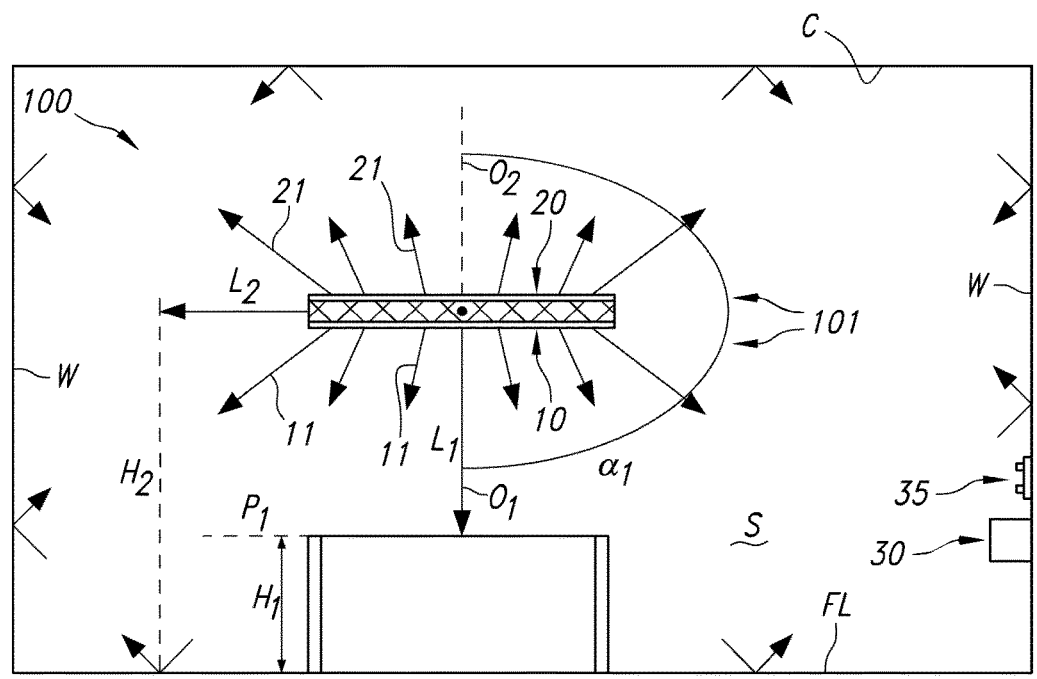
FIG. 10a schematically depicts an embodiment of the lighting system.

FIG. 10a schematically depicts an embodiment of the lighting system 100 comprising a first light source 10, a second light source 20, and optionally a control system 30.

The first light source 10 is configured to generate first light source light 11 with a controllable first radiant flux. The first radiant flux is dimmable over a first dimming range. The first light source light 11 has a first angular distribution relative to the lighting system 100, such as schematically depicted with the rays (arrows).

The second light source 20 is configured to generate second light source light 21 with a controllable second radiant flux. The second radiant flux is dimmable over a second dimming range. Further, the second light source light 21 has a second angular distribution relative to the lighting system 100, different from the first angular distribution.

Here, the light sources may be the same, but are directed to different directions. Hence, schematically an embodiment is depicted wherein the first light source light 11 has a first optical axis O1, wherein the second light source light 21 has a second optical axis O2, wherein the first light source 10 and the second light source 20 are configured to provide the first light source light 11 and the second light source light 21 with the optical axes O1,O2 having a mutual angle $\alpha 1 \neq 0°$ here having a mutual angle $90° \leq \alpha 1 \leq 180°$. In fact, in this schematically depicted embodiment $\alpha 1 = 180°$.

The system 100 may further comprise or be functionally coupled to the control system 30. The control system 30 is configured to control the first light source 10 and the second light source 20. As indicated above, in a controlling mode of the control system 30, the control system 30 is configured to control a value of one of the first radiant flux and the second radiant flux with a negative proportional dependence of a change in a value of the other of the first radiant flux and the second radiant flux over at least a respective part of the respective dimming range.

Reference 101 indicates lighting system light, which may comprise the first light source light and/or the second light source light, dependent upon the controlling mode.

FIG. 10a also schematically depicted an embodiment wherein the lighting system 100 further comprises a user interface 35 or is functionally coupled to such user interface. The user interface may thus at least be functionally coupled to the control system 30. The control system 30 may be configured to receive via the user interface 35 one or more of user instructions, such as (i) a total power of the lighting system light 101, (ii) a power of the first light source light 11, (iii) a power of the second light source light 21, (iv) a balance between the power of the first light source light 11 and the second light source light 21, (v) an application related parameter, etc.

The horizontal illuminance may especially be determined (or estimated) below the first light source and second light source, such as at desk level or at floor level. For instance, for a large room an average (horizontal) illuminance at desk height (selected from the range of 0.75-0.85 m) may be selected as horizontal illuminance, and an average wall illuminance may be choses as vertical illuminance.

The horizontal illuminance may e.g. be determined at a horizontal surface at a first height (indicated with reference H1) over the floor or bottom selected from the range of 0.0-1.0 m, such as at a first height of 0.75 m. The horizontal illuminance may be determined at a horizontal surface below the light sources, but may also be determined elsewhere in the space. For reference purposes, a position below the light sources may be used to determine a horizontal illuminance.

The vertical illuminance may especially be determined at a vertical surface at a second height (indicated with reference H2) over the floor or bottom selected from the range of 0.0-2.5 m, such as at a height selected from the range of 1-2 m, such as at 1.2 m. The vertical illuminance and the horizontal illuminance may be determined at the same position as well as at different positions. When determined at different positions, especially the vertical illuminance is determined at a second horizontal distance (indicated with reference L2) from the first light source and the second light source selected from the range of 0.5-5 m, such as 1-4 m, though other positions may also be chosen. For instance, this distance from the light sources may be determined in relation to the reference point (see also above).

As indicated above, other values may be chosen as well. Further, as indicated above for instance, the first illuminance may be the illuminance at floor level or at desk level, or, the first illuminance may be the ceiling illuminance, etc.

Figure 10B:
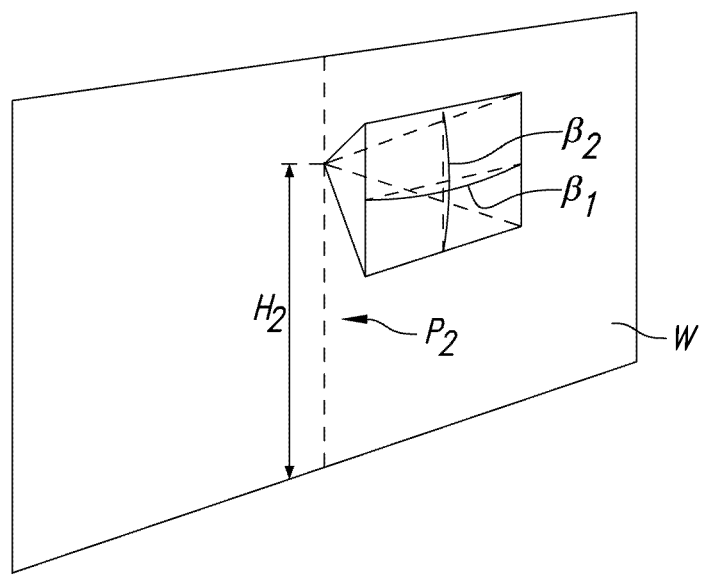
FIG. 10b schematically depicts a further aspect of the lighting system and its application.

FIG. 10b schematically depicts that the vertical illuminance may also be determined for specific illumination angles only. Hence, there may be an angular filter or weighing different angles of incidence on a vertical or horizontal surface. This is indicated with the angles $\beta 1$ and $\beta 2$. One may use an absolute angular filter, in the sense that only illuminance is evaluation based on illumination with light having an angle of incidence within the cone defined by $\beta 1$ and $\beta 2$. However, it may also be possible to weight different angels ($\beta 1$ and/or $\beta 2$) differently. For instance, the relevance of the angle may decrease with increasing angle relative to the normal. Note that this field of view is not necessarily symmetric with respect to the plane. The cutoff above is typically at a different angle than the cut-off below. Reference H2 indicates the height at which the illuminance may be evaluated.

The term "plurality" refers to two or more.

The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%.

The term "comprise" includes also embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices, apparatus, or systems may herein amongst others be described during operation. As will be clear to the person skilled in the art, the invention is not limited to methods of operation, or devices, apparatus, or systems in operation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A lighting system comprising a first light source, a second light source, and a control system, wherein:
the first light source is configured to generate first light source light with a controllable first radiant flux, wherein the first radiant flux is dimmable over a first dimming range;
wherein the first light source light has a first angular distribution relative to the lighting system;
the second light source is configured to generate second light source light with a controllable second radiant flux, wherein the second radiant flux is dimmable over a second dimming range; wherein the second light source light has a second angular distribution relative to the lighting system, different from the first angular distribution;
the control system is configured to control the first light source and the second light source, wherein, in a controlling mode of the control system, the control system is configured to control a value of one of the first radiant flux and the second radiant flux with a negative proportional dependence of a change in a value of the other of the first radiant flux and the second radiant flux over at least a respective part of the respective dimming range,
wherein the first light source is configured to generate the first light source light providing one or more of a first horizontal illuminance $E_{h1}$ and first vertical illuminance $E_{v1}$, wherein during operation of both the first and the second light source at equal power the second light source is configured to generate the second light source light providing one or more of a second horizontal illuminance $E_{h2}$ and second vertical illuminance $E_{v2}$, wherein $E_{h1} > E_{h2}$, and wherein $E_{v2} > E_{v1}$.

2. The lighting system according to claim 1, wherein the first light source light has a first optical axis (O1), wherein the second light source light has a second optical axis (O2), wherein the first light source and the second light source are configured to provide the first light source light and the second light source light with the optical axes (O1,O2) having a mutual angle $\alpha1 \neq 0°$.

3. The lighting system according to claim 2, having a mutual angle $90° \leq \alpha1 \leq 180°$.

4. The lighting system according to claim 1, wherein the first light source is configured as downlighter and wherein the second light source is configured as uplighter.

5. The lighting system according to claim 1, wherein the first light source light has a first optical axis (O1), wherein the second light source light has a second optical axis (O2), wherein the first light source and the second light source are configured to provide the first light source light and the second light source light with the optical axes (O1,O2) having a mutual angle $\alpha1 = 0°$.

6. The lighting system according to claim 1, wherein the first light source is configured to generate the first light source light providing the first horizontal illuminance $E_{h1}$ and the first vertical illuminance $E_{v1}$, wherein the second light source is configured to generate the second light source light providing the second horizontal illuminance $E_{h2}$ and the second vertical illuminance $E_{v2}$, and wherein in a controlling mode over at least part of one of the first dimming range and the second dimming range, a sum of the horizontal illuminances or a sum of the vertical illuminances is kept constant.

7. The lighting system according to claim 1, wherein the horizontal illuminance is defined as an illuminance at a horizontal surface at a first height (H1) over a floor or bottom selected from a range of 0.0-1.0 m, and wherein the vertical illuminance is defined as the illuminance at a vertical surface, at a second height (H2) over the floor or bottom selected from a range of 0.0-2.5 m.

8. The lighting system according to claim 1, wherein the first light source light has a first spectral composition, wherein the second light source light has a second spectral composition identical to the first spectral composition.

9. The lighting system according to claim 1, wherein the first light source light has a first spectral composition, wherein the second light source light has a second spectral composition, different from the first spectral composition.

10. The lighting system according to claim 9, wherein the lighting system is configured to generate in a controlling mode lighting system light comprising one or more of the first light source light and the second light source light, wherein the lighting system is configured to provide in a space wherein the lighting system is configured the lighting system light with a controllable first illuminance and a controllable second illuminance at spatially different positions in the space; wherein in a controlling mode of the control system the control system is configured to control a value of one of the first illuminance and the second illuminance, wherein one of the first illuminance and the second illuminance is maintained constant and wherein another of the first illuminance and the second illuminance is dimmed, wherein the first illuminance and the second illuminance are selected from the group consisting of photopic illuminance, cyanopic illuminance, chloropic illuminance, erytrhopic illuminance, rhodopic illuminance, and melanopic illuminance.

11. The lighting system according to claim 1, wherein the lighting system is configured to generate in a controlling mode lighting system light comprising one or more of the first light source light and the second light source light, wherein the lighting system further comprises a user interface functionally coupled to the control system, wherein the control system is configured to receive via the user interface one or more of user instructions selected from the group consisting of: (i) a total power of the lighting system light, (ii) a power of the first light source light, (iii) a power of the second light source light, (iv) a balance between the power of the first light source light and the second light source light, (v) an application related parameter, wherein the control system is configured to control in the controlling mode the first light source and the second light source in dependence of a predefined relation between the application related parameter and the negative proportional dependence, and wherein the application related parameter is defined on the basis of one or more of (a) a dimensions of space wherein the lighting system is applied, (b) a reflectivity of elements in the space wherein the lighting system is applied, and (c) a type of activities applied in the space; and wherein the lighting system comprises a luminaire, wherein the luminaire comprises the firsts light source and the second light source.

12. The lighting system according to claim 1, wherein the control system is further configured to receive during a calibration procedure a light sensor signal, and to control in the controlling mode the first light source and the second light source in dependence of a predefined relation between the light sensor signal and the negative proportional dependence.

13. The lighting system according to claim 1, wherein the lighting system is one of:
- a lamp unit comprising the controller and integrated first and second light source;
- a single luminaire comprising the controller and a housing accommodating at least one first light source and at least one second light source;
- a plurality of first modules comprising only first light sources and second modules comprising only second light sources;
- a plurality of lamp units and/or luminaires and at least one controller.

14. Use of the lighting system according to claim 1 for maintaining a first illuminance constant while varying a second illuminance, different from the first illuminance, wherein the first illuminance and the second illuminance are selected from the group consisting of horizontal illuminance and vertical illuminance.

15. Use according to claim 14, wherein the first illuminance and the second illuminance are selected from the group consisting of photopic illuminance, cyanopic illuminance, chloropic illuminance, erytrhopic illuminance, rhodopic illuminance, and melanopic illuminance and/or wherein one or more of the first illuminance and the second illuminance are evaluated in dependence of an angle of incidence on a relevant reference surface smaller than 90°.

* * * * *